(12) United States Patent
Gédet et al.

(10) Patent No.: US 9,795,426 B2
(45) Date of Patent: Oct. 24, 2017

(54) IMPLANTS

(71) Applicant: DePuy Synthes Products, Inc., Raynham, MA (US)

(72) Inventors: Philippe Gédet, Oberdorf (CH); Robert Frigg, Bettlach (CH)

(73) Assignee: DePuy Synthes Products, Inc., Raynham, MA (US)

( * ) Notice: Subject to any disclaimer, the term of this patent is extended or adjusted under 35 U.S.C. 154(b) by 555 days.

(21) Appl. No.: 13/789,422

(22) Filed: Mar. 7, 2013

(65) Prior Publication Data

US 2014/0257294 A1    Sep. 11, 2014

(51) Int. Cl.
*A61B 17/84* (2006.01)
*A61B 17/04* (2006.01)
(Continued)

(52) U.S. Cl.
CPC ........ *A61B 17/842* (2013.01); *A61B 17/0401* (2013.01); *A61B 17/683* (2013.01);
(Continued)

(58) Field of Classification Search
CPC ....... A61B 17/842; A61B 17/82; A61B 17/86; A61B 17/72; A61B 17/7216;
(Continued)

(56) References Cited

U.S. PATENT DOCUMENTS 2,829,414 A * 4/1958 Thomas ............... B64D 17/32
                                        24/265 AL
3,381,608 A    8/1974 Kletschka et al.
(Continued)

FOREIGN PATENT DOCUMENTS

DE    102007051783    5/2009
WO    WO 99/37219 A1    7/1999
(Continued)

OTHER PUBLICATIONS

Petersen et al., "Minar® Minimally INvasive Acromioclavicular Joint-Reconstruction," Endoworld, www.karlstorz.com, 2010, 12 pages.
(Continued)

*Primary Examiner* — Matthew Lawson
*Assistant Examiner* — Amy Sipp
(74) *Attorney, Agent, or Firm* — Baker & Hostetler LLP

(57) ABSTRACT

An implant assembly includes a first implant member, a second implant member, and a contractible element that is connected between the first and second implant members. The first implant member is configured to be placed against a first bone portion, and the second implant member is configured to be placed against a second bone portion. The contractible element is fixed at a first end to one of the first and second implant members, and movable at a second end with respect to one of the first and second implant members so as to induce tension in the suture, thereby providing a compressive force against the first and second bone portions. The second end can then be fixed with respect to the first and second implant members. The contractible element can contract in length in response to bodily fluids, thereby ensuring adequate post-operative compression. An instrument is also disclosed that is configured to implant the first and second implant members adjacent the first and second bone portions, respectively.

9 Claims, 11 Drawing Sheets

(51) Int. Cl.
*A61B 17/68* (2006.01)
*A61B 17/88* (2006.01)
*A61B 17/00* (2006.01)
*A61B 17/80* (2006.01)

(52) U.S. Cl.
CPC ....... *A61B 17/8061* (2013.01); *A61B 17/8872* (2013.01); *A61B 2017/00898* (2013.01); *A61B 2017/0404* (2013.01); *A61B 2017/0409* (2013.01); *A61B 2017/0414* (2013.01); *A61B 2017/0453* (2013.01); *A61B 2017/0458* (2013.01); *A61B 2017/0496* (2013.01)

(58) Field of Classification Search
CPC ............ A61B 17/7225; A61B 17/0487; A61B 17/0466; A61B 2017/681; A61B 2017/7053; A61B 2017/7055; A61B 2017/0496; A61B 2017/0446–2017/0454; A61B 2017/0414; Y10T 24/3969; Y10T 24/3978
USPC ....................................................... 24/136 B
See application file for complete search history.

(56) References Cited

U.S. PATENT DOCUMENTS

| | | | |
|---|---|---|---|
| 3,931,821 A | 1/1976 | Kletschka et al. | |
| 4,590,928 A | 5/1986 | Hunt et al. | |
| 5,306,301 A | 4/1994 | Graf et al. | |
| 5,415,658 A * | 5/1995 | Kilpela et al. | 606/300 |
| 5,921,986 A * | 7/1999 | Bonutti | A61B 17/0401 606/215 |
| 6,533,802 B2 | 3/2003 | Bojarski et al. | |
| 7,070,601 B2 | 7/2006 | Culbert et al. | |
| 8,142,434 B2 * | 3/2012 | Bluechel | 606/74 |
| 8,231,674 B2 | 7/2012 | Albertorio et al. | |
| 2002/0133179 A1 | 9/2002 | McDevitt et al. | |
| 2006/0167553 A1 | 7/2006 | Cauthen, III et al. | |
| 2006/0217711 A1 | 9/2006 | Stevens et al. | |
| 2007/0250059 A1 * | 10/2007 | Weisshaupt | A61B 17/683 606/60 |
| 2008/0140093 A1 * | 6/2008 | Stone | A61B 17/0401 606/144 |
| 2008/0208223 A1 * | 8/2008 | Kraemer | A61B 17/82 606/151 |
| 2008/0281355 A1 * | 11/2008 | Mayer | A61L 17/00 606/228 |
| 2010/0241164 A1 | 9/2010 | Fischer et al. | |
| 2010/0256612 A1 * | 10/2010 | Dell'Oca | A61B 17/82 606/1 |
| 2010/0318137 A1 * | 12/2010 | Stucki | A61B 17/8066 606/324 |
| 2011/0022061 A1 * | 1/2011 | Orphanos | A61B 17/0401 606/139 |
| 2012/0116450 A1 | 5/2012 | McDevitt et al. | |
| 2012/0215224 A1 * | 8/2012 | Songer | A61B 17/842 606/74 |
| 2013/0158609 A1 | 6/2013 | Mikhail et al. | |
| 2014/0005729 A1 * | 1/2014 | DiMatteo | 606/281 |

FOREIGN PATENT DOCUMENTS

| | | |
|---|---|---|
| WO | WO 2009/126227 A2 | 10/2009 |
| WO | WO 2012/167138 A1 | 12/2012 |

OTHER PUBLICATIONS

Sacaral Bar Kit Technique Guide, Synthes®, www.synthes.com, 2000, 8 pages.

Kang et al., "Robotic knot tying in minimally invasive surgeries," Proceedings of the 2002 IEEE/RSJ Intl. Conference on Intelligent Robots and Systems, Oct. 2002, 1421-1426.

Arthrex, "TightRope®", http://www.arthrex.com/foot-ankle/tightrope, Accessed on Feb. 8, 2013, 3 pages.

* cited by examiner

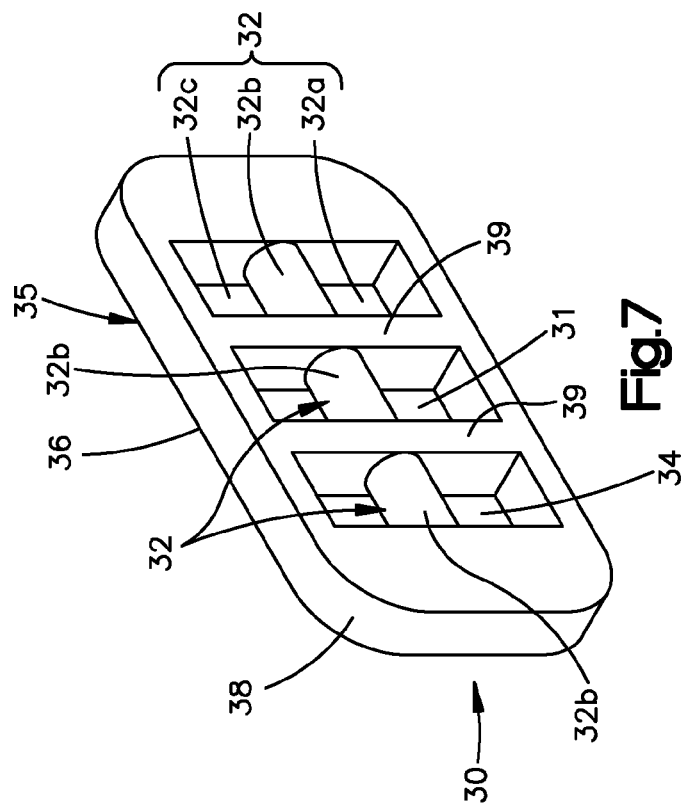
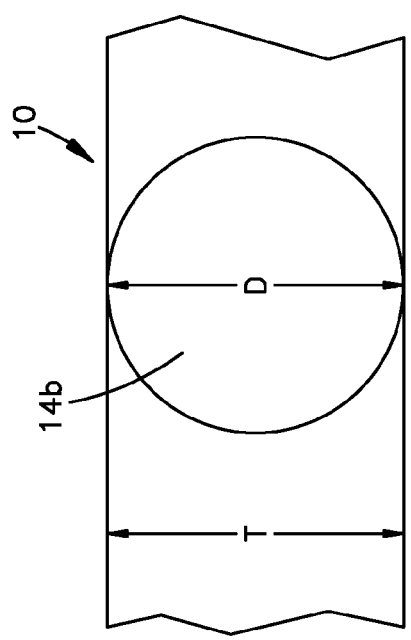
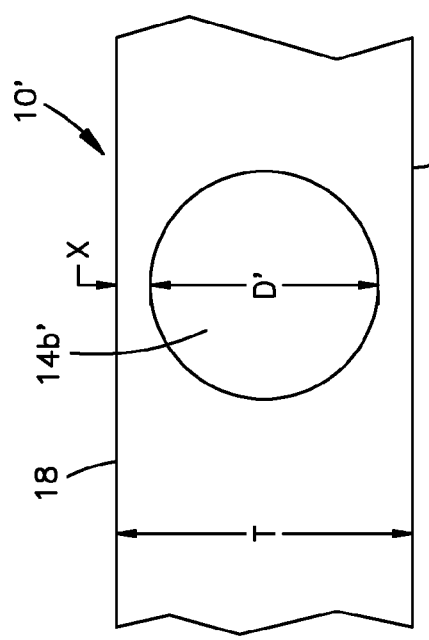

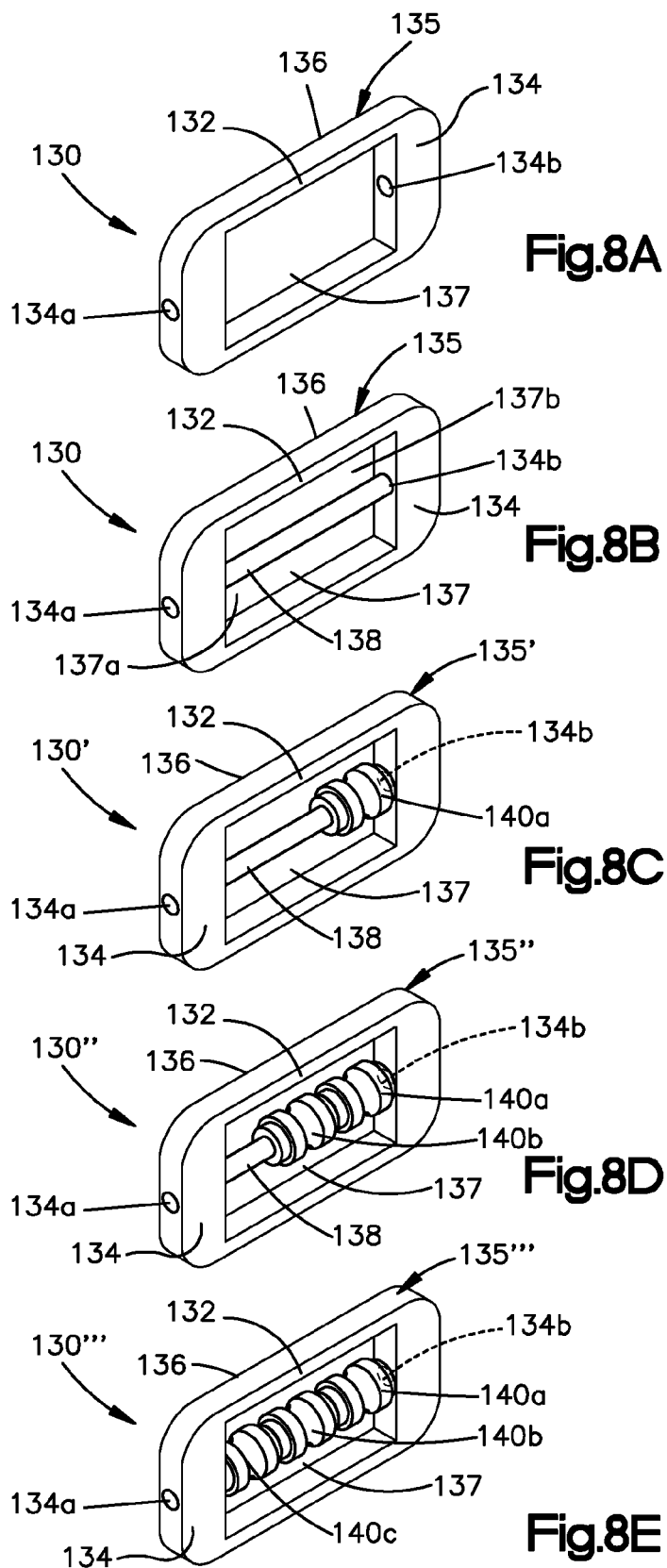

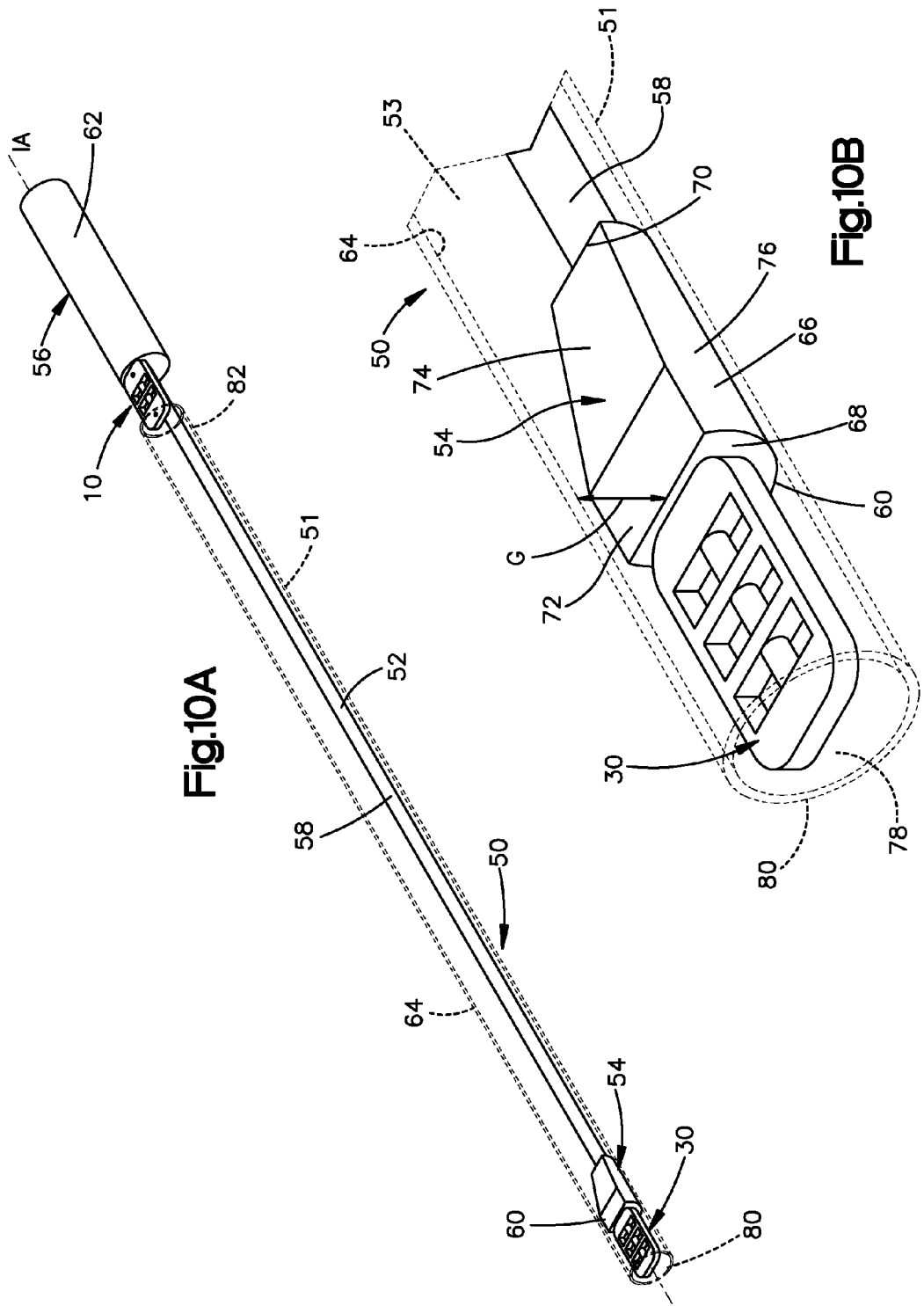

IMPLANTS

FIELD OF DISCLOSURE

The present disclosure relates to implants, instruments, methods of implantation and methods of manufacture.

BACKGROUND

Implants for holding together portions of a bone to support bone healing are known. For instance, FIG. 11 shows an example of a conventional implant. The implant, commercially available from DePuy Synthes®, having a place of business in West Chester, Pa., is used to hold together fractured portions of a sacrum. The implant can include one or more rod assemblies 200, each having a rod 201 that extends through first and second opposed portions 12 and 11 of the ilium, respectively, that are positioned on opposed medial-lateral sides of the sacrum S. The rod can be threaded, and configured to threadedly receive respective first and second nuts 202 and 204 at its opposed first and second ends. The first and second nuts 202 and 204 can be threaded onto the rod 201, and compressed against the first and second portions 12 and 11 of the ilium so as to provide a compressive force to a fractured sacrum S. The implant can further include a first washer 206 disposed between the first nut 202 and the first portion 12 of the ilium, and a second washer 208 disposed between the second nut 204 and the second portion 11 of the ilium.

FIG. 12 shows another conventional implant that uses compression to hold bone portions together during a healing process. The implant illustrated in FIG. 12 is used for syndesmosis fixation, and is commercially available under the product name TightRope® from Arthrex, Inc., having a place of business in Napes, Fla. The implant illustrated in FIG. 12 includes a bone plate 210 and a button 212 that are disposed on opposite sides of bone. The bone plate 210 is anchored to the bone using one or more screws 214, and a suture 216 is drawn through the bone from the button 212 to the bone plate 212 and fastened to the bone plate 212 to provide compression to the bone.

Yet another conventional implant shown in FIG. 13 uses compression to support a healing process of the acromioclavicular (AC) joint. The implant illustrated in FIG. 13 is the MINAR® system, commercially available from Karl Storz GmbH & Co. KG, having a place of business in Berlin, Germany. The implant of FIG. 13 can include first and second buttons 218 and 220 that are disposed on opposed surfaces of the clavicle 217 and the coracoid process 219, respectively, and a suture 221 that extends through the first button 218, through the AC joint and wraps around the second button through first and second apertures, respectively, and is drawn again through the AC joint and through the first button 218. The suture 221 can be fastened to the first button such that the suture 221 provides compression between the first and second buttons 218 and 220, and thus provides compression between the clavicle and the coracoid process.

A problem common to all these systems is that once implanted and without additional surgery it is complicated to adjust the implant to, for example, maintain the compressive force supporting the healing process.

SUMMARY

In a first aspect, an implant assembly has a first implant member, a second implant member and a contractible element. The contractible element spans between the first implant member and the second implant member. The contractible element has a first end fixed to one of the first and second implant members and a second end adjustably fixable to a fixing arrangement provided on one of the first or second implant members.

The fixing arrangement may be provided on the implant member to which the first end of the contractible element is fixed.

The second end of the contractible element may be fixed to the first implant and adjustably fixable to the fixing arrangement that is located on the first implant member.

The fixing arrangement may have an adjustment region in which the contractible element is adjustable relative to the implant member.

The fixing arrangement may comprise a fixing region in which the second end of the contractible element is fixable with one or more of a knot, a crimp, a cam-lock, a set screw or a clamp The contractible element may be capable of self-contracting. The contractible element may be thread-like and have a core surrounded by a mesh. The contractible element may have a first length measured from the first end to the second end. The swelling of the core may cause the mesh to expand causing the contractible element to contract from the first distance to a second shorter distance. The swelling of the core may occur due to exposure of the core to bodily fluids.

The fixing arrangement may have an adjustment region. The adjustment region may have a channel defined in the implant member through which the second end of the contractible element may be passed.

The contractible element may be thread-like. At least one pulley may be arranged in one of the first or second implant members. The thread-like contractible element may be looped from the first end fixed in the first implant member to the adjustably fixable second end arranged in one of the first or second implant members through at least one pulley located in one of the first and second implant members. In particular, the first end of the thread-like contractible element may be fixed in the first region to the first implant member, looped between a plurality of pulleys arranged in the first and second implant members and adjustably fixable to the fixing arrangement provided on the first member.

The implant member with the pulley may have a first channel and a second channel. The or each channel may define a first opening on a first surface of the implant member and a second opening on a second surface of the implant member. The pulley may be defined by a smooth transition between the first openings and/or the second openings.

In a second aspect of the present invention there is provided an implant assembly. The implant assembly may have a first holder and a second holder for holding a suture in a fixed position relative to the implant member. The first holder may be arranged to fixedly hold the suture. The second holder may be arranged to adjustably hold the suture.

In a third aspect of the present invention there is provided an implant assembly. The implant assembly may have a plurality of pulleys. The pulleys may be arranged to receive and hold a suture.

In a fourth aspect of the present invention there is provided a suture holding mechanism. The suture holding mechanism may have a locking element deployable between an open configuration in which a suture may move relative to the suture holding mechanism and a closed configuration in which the suture is immovable relative to the suture holding mechanism.

The suture holding mechanism may have a first channel in which a suture may be arrangeable. The locking element may be moveable in a direction which is transverse to a channel axis of the first channel between the open and closed configurations. In the open configuration, the suture may be moveable relative to the first channel. In the closed configuration, the suture may be immovable relative to the first channel. In the closed configuration, when compared with the open configuration more of a leading end of the locking element may be located in the first channel. In use with a suture positioned in the first channel, a closed configuration occurs when the amount of the leading end located in the channel restricts movement of the suture relative to the first channel. In this configuration, the leading end presses the suture against a wall forming the first channel to hold the suture in position relative to the first channel. In a completely extended position, the locking element may extend across the first channel and the leading end may abut the wall defining the first channel.

The suture holding mechanism may have a deployment mechanism arranged to deploy the locking element between the open and closed configurations. The deployment mechanism may have a moveable element engageable with the locking element. Movement of the moveable element in a first direction may engage a first end of the moveable element with a trailing end of the locking element to deploy the leading end into the first channel. The moveable element may be a set screw. The set screw may have a tapered end and the trailing end may be angled to correspond to the angle forming the tapered end.

In a fifth aspect of the present invention there is provided an instrument for inserting an implant assembly of the first aspect. The instrument has a body having a chamber for housing the implant assembly, an opening into the chamber and an external surface shaped and dimensioned to be passed through boreholes formed in a bone. The instrument has a deployment element moveable between a first position and a second position relative to the chamber. The deployment element having an implant engaging member. When an implant assembly is housed in the chamber, movement of the deployment element from the first position to the second position engages the implant engaging member with the implant assembly to move at least part of the implant assembly out of the chamber through the opening.

An external surface of the instrument may have drilling flutes for making boreholes in a bone.

In a sixth aspect of the present invention there is provided a method of treating a musculoskeletal condition. The method may comprises one or more steps, which may involve:

selecting an implant assembly having a first member, a second member and a self-contracting element connecting the first member to the second member;

implanting the implant assembly in an arrangement, the arrangement selected to treat the musculoskeletal condition;

tensioning the self-contracting element to set an initial compression that the first and second members apply to a location to treat the musculoskeletal condition, the location being a location of the musculoskeletal condition; and maintaining a compression post-operatively during the treatment of the musculoskeletal condition;

The compression may be maintained post-operatively through interaction of the self-contractible element with bodily fluids that activate a self contracting feature of the self contracting element. The initial compression may be a compression determined as being necessary for treating the musculoskeletal condition. The compression maintained post-operatively may be substantially the same as the initial compression. The treatment of musculoskeletal condition may involve treating, for example, of a bone fracture, a torn or ruptured ligament, and a torn AC-CC Joint.

A tension applied to the self-contracting element may cause the compression that the first and second members apply to the location. The tensioning step may involve:

identifying when a tension applied to the self-contracting element may cause the initial compression; and setting the initial compression by fixing the self-contracting element to the first implant.

The tensioning step may involve checking a tension applied to the self-contracting element with a tension measurer.

The step of implanting may include arranging the implant assembly in the arrangement by:

positioning the second implant at a respective position adjacent the location;

positioning the first implant at a respective position adjacent the location, the respective position corresponding to the first implant being different than the respective position corresponding to the second implant, and selected so that the initial compression applied to the location by the first and second implants is appropriate for the treatment of the musculoskeletal condition.

The step of implanting may include the step of positioning an instrument containing the implant assembly adjacent the location and manipulating the instrument to arrange the implant assembly in the arrangement.

The step of positioning an instrument may involve positioning the instrument through one or more holes formed in musculoskeletal tissue, preferably, through holes formed in a bone portion or a plurality of bone portions. The holes may be formed by drilling through the musculoskeletal tissue. The instrument may have a container for holding the implant assembly. The step of positioning the instrument may involve positioning the container adjacent the location.

The instrument may have a deployer arranged to position the first and second members of the implant assembly. The step of manipulating the instrument may involve:

moving the deployer to position the second implant at a first position adjacent the location; and moving the deployer to position the first implant at a respective position adjacent the location, the respective position of the first implant being different than the respective position of the first implant, and selected so that the initial compression applied to the location by the first and second implants is appropriate for the treatment of the musculoskeletal condition.

The instrument may have a container for holding the implant assembly. The step of manipulating may involve deploying the first and second implants out from the container. The container may have a first opening and a second opening and the step of manipulating may involve the step of deploying the first implant through the first opening and the second implant through the second opening. The instrument may have a deployer arranged to position the first and second members of the implant assembly and the first and second openings may be connected by a channel. The step of manipulating may involve translating the deployer along the channel in a first direction to position the first implant at a first position adjacent the location through the first opening. The step of manipulating may involve translating the deployer along the channel in a second direction to position the second implant at a second position adjacent the location through the second opening.

The method may further include the step of removing the instrument after the implant assembly is implanted in the arrangement.

In a seventh aspect of the present invention there is provided a method of manufacturing an implant assembly. The method may involve the step of taking a first implant member and a second implant member, and connecting a self-contracting element to the first and second implant members.

The self-contracting element may be a thread-like element, and each one of the first and second implant members may have a pulley arrangement. The connecting step may involve threading the thread-like self-contracting element through the pulley arrangement. The first implant member may have a first holder for holding a first end of the thread-like self-contracting element. The implant member may have a second holder for holding a second opposed end of the thread-like self-contracting element. The thread-like self-contracting element may be adjustably held by the second holder.

In an eight aspect of the present invention there is provided a method of deploying an implant assembly from an instrument and may involve the steps of:
    selecting an instrument containing the implant assembly, the instrument having a channel and a deployment element moveable between a first position and a second position relative to the channel;
    moving the deployment element from the first position to the second position during which the deployment element engages with the implant assembly and pushes the implant assembly out of the channel.

The moving step may involve pushing a portion of the implant assembly out of the channel.

The implant assembly may have a first member and a second member. The step of moving the deployment element may involve engaging the deployment element with the second member and pushing the second member out of the channel through an exit point as the deployment element is moved from the first position to the second position. The first member may remain in the channel whilst the second member is being pushed out of the channel.

The implant assembly may have a first member deployable separately from the second member. The step of moving the deployment element may involve the deployment element engaging with the second member and pushing the second member out of the channel through an exit point as the deployment element is moved from the first position to the second position. The first member may remain in the channel whilst the second member is being pushed out of the channel.

The implant assembly may have a first member and a second member removable separately from the channel through an exit point of the channel. The exit point through which the first and second members may be removed from the channel may be the same exit point.

The implant assembly may have a first member and a second member removable separately from the channel. The method may further involve removing the first member from the channel by drawing the instrument over the first member. The instrument may be drawn over the first member after the deployment element has been moved to the second position. The instrument may be drawn over the first member after the second member has been pushed out of the channel.

The implant assembly may have a first member and a second member. The method may further involve the step of:
    arranging a portion of the instrument at a deployment site before the moving step;
    the moving step may involve deploying the implant assembly at the deployment site; and
    withdrawing the instrument from the deployment site after the moving step.

The implant assembly may have a first member and a second member. The method may further involve the step of:
    arranging a portion of the instrument at a first deployment site before the moving step;
    moving the deployment element from the first position to the second position to deploy the second member at the first deployment site; and
    drawing the instrument over the first member to deploy the first member at a second deployment site, which is preferably different to the first deployment site.

The method may further involve a step of positioning the instrument through at least one hole in musculoskeletal tissue before the moving step. The at least one hole may be bore hole through a bone portion. The at least one hole may include a first and a second hole, the first hole may be a hole through a first bone portion and the second hole may be a hole through a second bone portion. The first hole may be located in an Ilium crest situated on one side of the sacrum and a second hole may be located in an Ilium crest situated on the other side of the sacrum.

The implant assembly may have a self-contracting element connecting a first member to a second member. The self-contracting element may have a fluid activatable feature which acts against the tendency to be stretched.

In a ninth aspect of the present invention there may be provided a method of fixing a thread like element to an implant. The method may involve:
    pulling the thread-like element through a channel in the implant assembly, the implant assembly having a holder; and
    fixing the thread-like element to the holder thereby preventing movement of the thread-like element relative to the channel.

In a tenth aspect of the present invention there may be provided a method of maintaining compression between a first implant member and a second implant member, the method involve the steps of:
    selecting a first implant member and a second implant member that are connected to each other by a self-contracting element;
    arranging the first implant member to abut a first surface and the second implant member to abut a second surface;
    tensioning the self-contracting element to set an initial compression applied to the first and second surfaces by the first and second implants;
    maintaining a post-setting compression through interaction of the self-contracting element with fluids that activate a self contracting feature of the self contracting element.

The post setting compression may be substantially the same as the initial compression.

BRIEF DESCRIPTION OF THE DRAWINGS

One or more embodiments of the present disclosure will now be described below with reference to the accompanying drawings, in which:

FIG. 6A is a partial sectional side view of the first plate of FIG. 4, taken along line A-A;

FIG. 6B is a partial sectional side view of the first plate as illustrated in FIG. 6A, but constructed in accordance with an alternative embodiment;

FIG. 7 is a perspective view of the second plate of the implant assembly of FIG. 1;

FIG. 8A is a perspective view of a frame of alternative embodiments of the second plate of FIG. 1;

FIG. 8B is a perspective view of a first alternative embodiment of the second plate of FIG. 1, including the frame shown in FIG. 8A;

FIG. 8C is a perspective view of a second alternative embodiment of the second plate of FIG. 1, including the frame shown in FIG. 8A;

FIG. 8D is a perspective view of a third alternative embodiment of the second plate of FIG. 1, including the frame shown in FIG. 8A;

FIG. 8E is a perspective view of a fourth alternative embodiment of the second plate of FIG. 1, including the frame shown in FIG. 8A;

FIG. 10A is a perspective view of an instrument configured to insert the implant assembly of FIG. 1;

FIG. 10B is an enlarged perspective view of a first end of the instrument of FIG. 10A;

DETAILED DESCRIPTION

Figure 1:
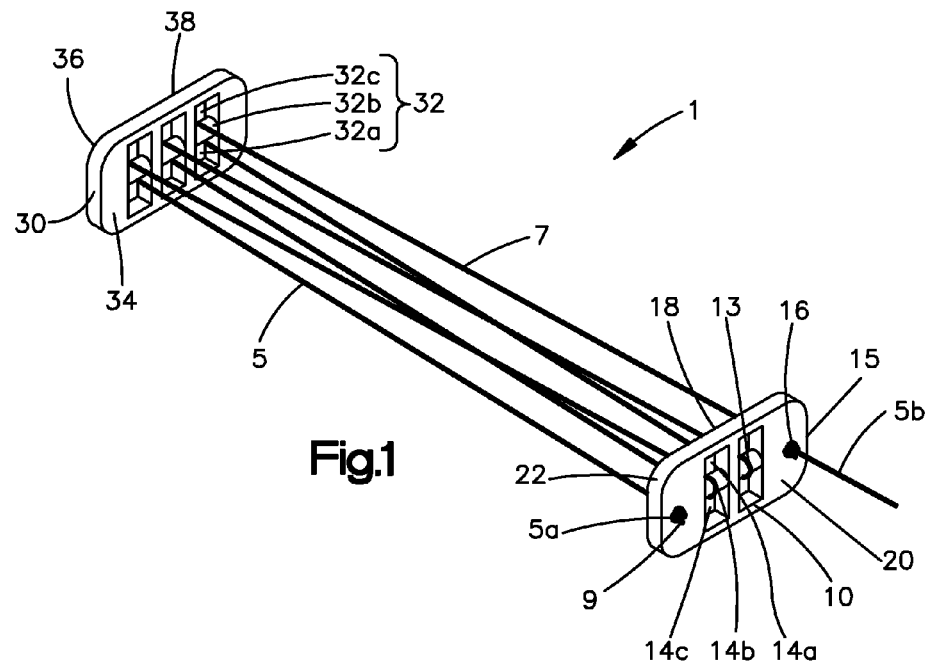
FIG. 1 is a perspective view of an implant assembly including first and second plates, and a contractible element joined to the first and second plates, in accordance with one embodiment.

Referring to FIGS. 1 to 10D generally, an implantation system constructed in accordance with one embodiment includes one or more implant assemblies 1 and an instrument 50 configured to implant the implant assemblies 1 into a patient's body. The implant assemblies 1 can each include a first implant member, which could be in the form of a first plate 10, a second implant member, which could be in the form of a second plate 30, and a contractible element 5 that is linked to the first and second plates 10 and 30, respectively. In use, the first plate 10 may be deployed relative to a first portion of musculoskeletal tissues, for example a first bone portion 12, and the second plate 30 may be deployed relative to a second portion of musculoskeletal tissues, for example a second bone portion 11. The first bone portion 12, for instance, can be the ilium bone of the right hip, and the second bone portion 11 can be the ilium bone of the left hip.

The first and second bone portions 12 and 11, respectively, can be opposed first and second portions of an ilium that are separated by a sacrum S, and thus opposed on opposite sides of the sacrum S. The contractible element 5 may then be adjusted so that the first plate 10 and second plate 30 are arranged to abut and apply a compressive force to the respective first and second bone portions 12 and 11, respectively. The contractible element 5 is configured to interact with bodily fluids after implantation, such that the contractible element 5 self-contracts after implantation so as to maintain the compressive force as will be described in more detail below.

Figure 2A:
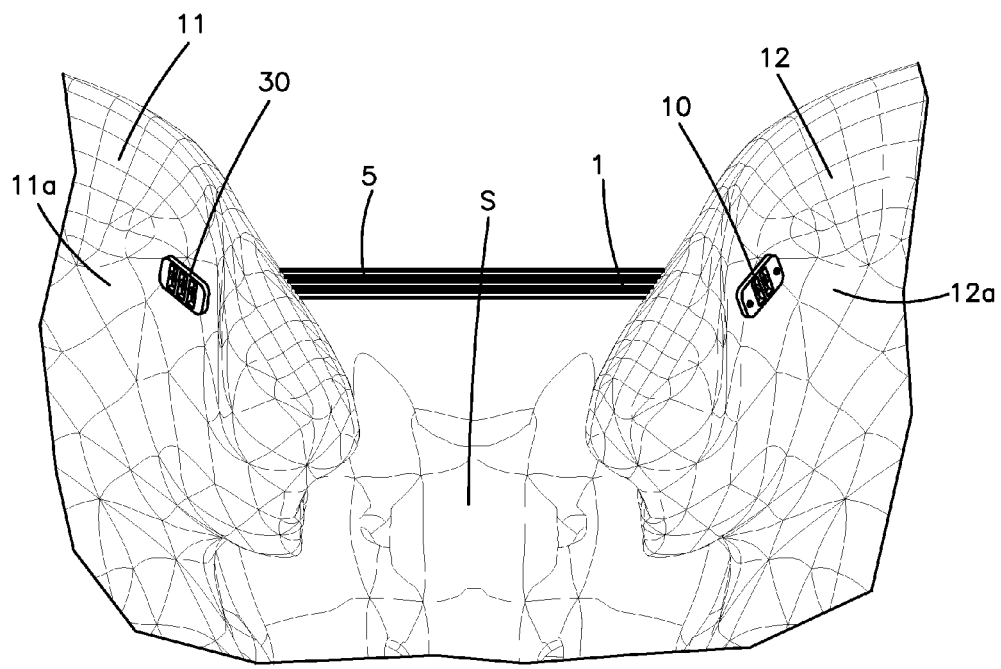
FIG. 2A is a schematic view of the implant assembly illustrated in FIG. 1 implanted on first and second portions of an Ilium.
Figure 2B:
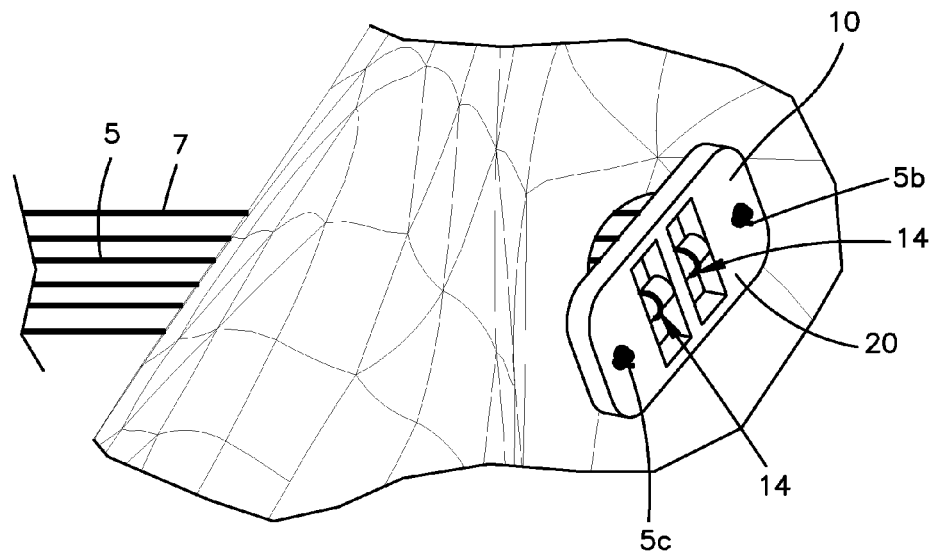
FIG. 2B is another schematic view of the first plate of the implant assembly of FIG. 1, shown implanted on first portion of the Ilium.
Figure 2C:
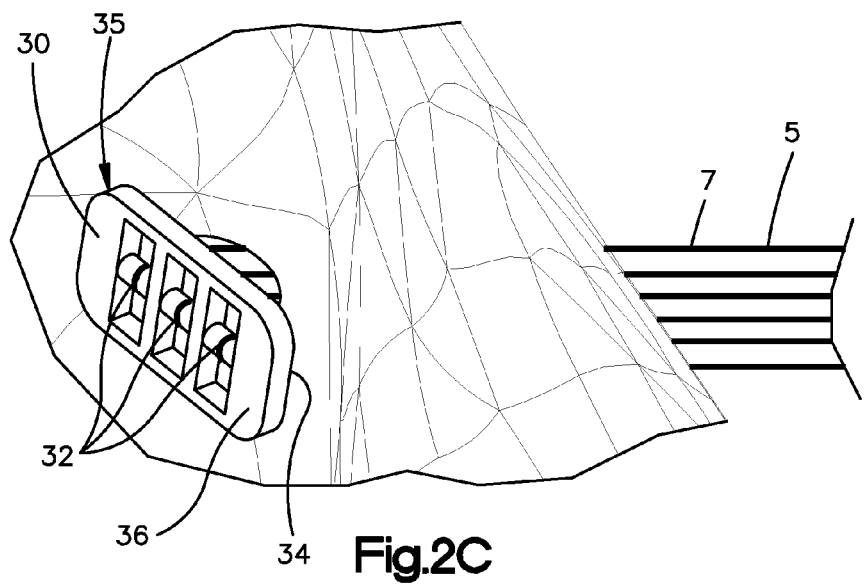
FIG. 2C is another schematic view of the second plate of the implant assembly of FIG. 1, shown implanted on second portion of the Ilium.
Figure 3:
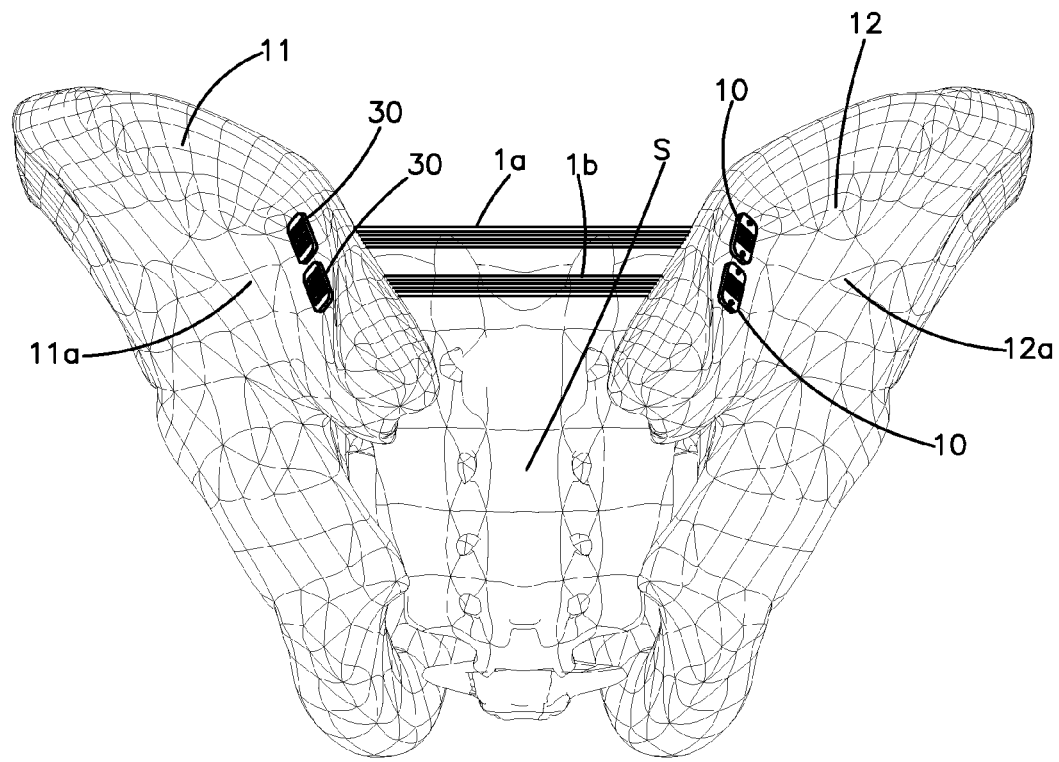
FIG. 3 is a schematic view of first and second implants of the type illustrated in FIG. 1, shown implanted on first and second portions of an Ilium.

Referring to FIGS. 2A to 2C a particular use of the implant assembly 1 is shown from a posterior view of the sacrum and Ilium. The implant assembly 1 is positioned to apply a compressive force to the Ilium on the right and left side of the sacrum. In particular, the first plate 10 is positioned on the lateral surface 12a of the first bone portion 12, which can be the ilium bone on the right hip, as described above. The second plate 30 is positioned on the lateral surface 11a of the second bone portion 11, which can be the Ilium bone on the left hip as described above. The first and second plates 10 and 30 are configured to apply compression to the lateral surfaces 12a and 11a so as to maintain compressive pressure on the sacrum bone S that is disposed between the first and second bone portions 12 and 11 of the Ilium. When the sacrum S is fractured, the compression is used to promote bone healing. Since the implant assembly 1 has the ability to maintain the compressive force throughout bone healing, the reduction of the fracture is maintained and bone healing promoted. That is, the maintenance of the compressive force may counteract or resist a tendency of the first plate 10 and second plate 30 to creep away from each other due to the various factors, such as, bodily fluids, soft tissue movement, stretching of traditional sutures and bone movement that may act upon the implant whilst implanted in situ. As illustrated in FIG. 3, the implantation system can include first and second implant assemblies 1a and 1b, which can each be constructed as described herein with respect to the implant assembly 1, and can be positioned at different locations relative to an Ilium crest to apply a compressive force to the sacrum S.

The implant assembly 1 has a suture, or other suitable thread-like element, as the contractible element 5. The suture 7 has a first fixed end 5a and a second tensioning free end 5b and is elongate along a longitudinal axis. The suture 7 is capable of self contracting to reduce a distance between the fixed end 5a and the free end 5b with respect to the longitudinal axis. Such a suture 7 is disclosed is U.S. Patent Publication No. 2008/0281355, the disclosure of which is expressly incorporated herein in its entirety by reference. In particular, the suture 7 has a core surrounded by a mesh of, for example, threads arranged helically around the core, in particular braided or interlacing threads, such as textile threads typically used for monofilament or multifilament suture materials. In particular, threads of known suture materials, such as those typically used in surgical suture materials, may be used. For example, the threads may be stretched polyesters, polyamides, polyolefins, polyaramides, expanded or densely halogenated polymers or high-strength ladder polymers such as polyetherether ketone, captones, polyurethanes, PUR, siloxane, PEG or other permeable, in particular semi permeable products in the form of osmotic, elastic or plastic and geometrically extendible membranes (e.g. stretching of axial folds, pleats or undulations).

Referring now to FIG. 1, the contractible element 5 can be configured as a suture 7 that can have a rest state in which it is inactive, i.e., a state when it is not self-contracting. The suture 7 can be elongate along a longitudinal direction between the first and second plates 10 and 30, and can include a core and a mesh that surrounds the core. The mesh can define threads such that, when the suture 7 is in the rest state, the threads of the mesh surrounding the core can be interwoven and angularly offset with respect to the longitudinal direction of the suture 7. For instance, the threads of the suture can be oriented, for example, at an angle of between 5 and 50 degrees, for example 30 degrees, with respect to the longitudinal direction of the suture 7. The core 41 is a material swellable from a first thickness to a greater second thickness to transition the threads to a contracted state. The swelling of the core results in the angle of the threads of the mesh increasing with respect to the longitudinal direction and with respect to the angle at which they are orientated in the rest state. For example, if in the rest state the threads were angled at 30 degrees in the contracted state the threads could be at an angle greater than 30 degrees for, for example, at angle between 35 to 50 degrees, for example, 45, 46, 47 and 48 degrees. In the contracted state, the distance between opposed sides of the mesh has increased, which results in a contraction of the suture in the longitudinal direction.

The swelling of the core can be caused by one or both of chemical and physical processes. The swelling process can be achieved, for example, by the core being osmotic. That is, the core can have an osmotically active substance (for example salt, particulate form of a water-soluble substance (for example saccharides) or highly concentrated solution of these substances in an elastic tube), which accordingly is configured to receives and retain (for instance absorb or adsorb) water. The osmotically active substances may also include biocompatible inorganic salts and aqueous solutions thereof, for example sodium chloride (NaCl) or calcium chloride, calcium carbonate, tricalcium phosphate, or organic, osmotically active molecules can be used, for example low-molecular-weight polysaccharides such as dextran. In a particular example, the core may have a filamentary polymer material, for example a thermoplastic elastomer (polyurethane, polyester), a crosslinked elastomer (silicone, polyurethane, elastin, collagen) or a gel (polyethylene glycol, alginate, chitosan) in which salt crystals are incorporated. To improve handling and to further influence the kinetics of osmosis, the osmotically active substances can also be embedded in a biocompatible gel or hydrogel (for example from the group of alginates, chitosans or copolymers thereof, polyacrylates, polyethylene glycol, etc.) or, as explained above, in an elastomer. In addition, the core may be made up of several membrane-like layers or can also be provided with stable or soluble diffusion-inhibiting layers. If hydrogels are used, such a membrane-like property can also be achieved by means of a crosslinking density that increases considerably toward the outside. The concentration differences effecting osmosis are to be achieved between thread core and surrounding blood or interstitial and/or intrastitial fluid of the patient.

Figure 4:
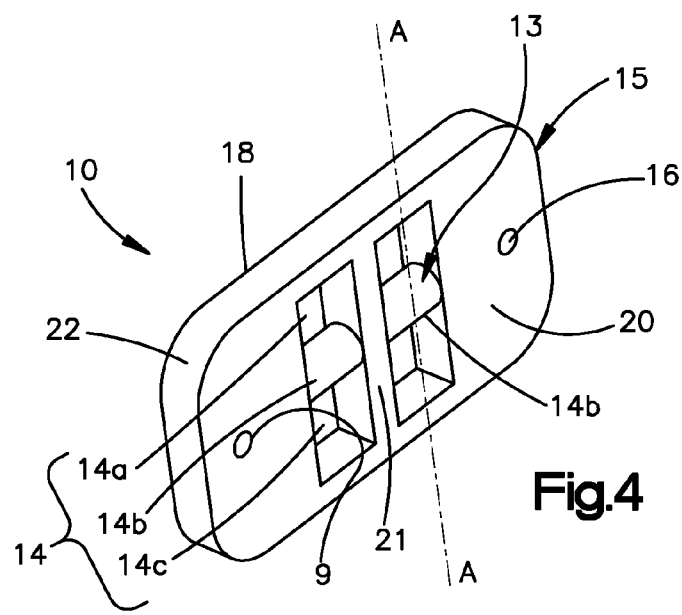
FIG. 4 shows a perspective view of the first plate of the implant assembly shown in FIG. 1.

Referring now to FIG. 4, the first plate 10 includes a first plate body 15 that defines a first surface 18, a second surface 20 opposite the first surface 18, and an edge 22 that is connected between the first surface 18 and the second surface 20. The first plate 10 includes a first holder 9 supported by the first plate body 15, a pulley arrangement 13 supported by the first plate body 15, and a fixing arrangement such as a second holder 16, supported by the first plate body 15. The edge 22 defines an outer perimeter of the first plate 10, and the first plate defines a plate thickness T that extends from the first surface 18 to the second surface 20. The first plate 10 can define a substantially cuboid shape with a rectangular cross-section whose corners are rounded to, for example, minimize soft tissue irritation. The first plate 10 can define a length as measured along its major axis as desired, such as approximately 20 mm. The first plate 10 can define a width measured along its minor axis as desired, such as approximately 7 mm. The thickness T as measured from the first surface 18 to the second surface 20 can be as desired, such as approximately 2 mm. However, as the skilled person would of course understand other dimensions are of course possible. For example, in treatment of a torn Syndesmosis joining the tibia to the fibula or a torn AC joint the length, width and depth could be approximately 12 mm, approximately 5 mm and approximately 1.5 mm, respectively.

The first holder 9 is configured to fixedly hold a fixed end 5a of the suture 7 in position and defines a starting point from which the suture 7 is threaded around the pulley arrangement 13 to the second holder 16. In one embodiment, the first holder 9 can be configured as a channel that extends between the first and second surfaces 18 and 20, and defines respective apertures that extend into the first and second surfaces 18 and 20. Thus, the aperture can extend through the first plate body 15 from the first surface 18 to the second surface 20. The implant assembly 1 can include a holding arrangement that includes the first holder 9 in combination with a holding element 5c (see FIG. 2B) supported by the suture 7. For instance, the holding element 5c can be defined on or by the suture 7. The holding element 5c could be a stopper 5c. As shown by FIG. 2C, the stopper 5c could be an annulus formed around the fixed end 5a having a diameter greater than the diameter of the channel of the first holder 9. That is, the stopper 5c, which can be an annulus, is dimensioned so that it abuts the first or second surface 18 or 20, respectively, of the first plate 10 in a region surrounding the respective aperture of the first holder 9, thereby preventing the fixed end 5a being pulled into the channel. The stopper can be formed of any suitable material. As the skilled person would understand, the stopper can be a suitable resilient or plastically deformable material such as metals, for example, stainless steel, and polymers.

Other holding mechanisms capable of holding the fixed end 5a in a fixed position relative to the first plate 10 are of course possible as the skilled person would understand. The holding element could be another stopper variant. For example, the holding element could be a plug arranged on the fixed end 5a that is shaped to be pulled into the channel and interfere with the wall of the channel to form an interference fit to prevent the fixed end 5a from being pulled through the channel and thereby prevent the fixed end 5a moving relative to the first plate 10. The plug has an insertion end and a trailing end. The plug is shaped to define a taper having its widest point at the trailing end such that when the insertion end is pulled into the channel the plug may increasingly interfere and may have a truncated cone shape. Similarly to the stopper described above, the plug may be formed from a plastically deformable biocompatible material such that when the plug is disposed in situ in the channel it tends to resist the compressive forces applied to it by the channel and thereby maintain the interference fit. In another example, the holding element could be a stopper in the form of an element crimped onto the fixed end 5*a*. The crimp is dimensioned to abut the first or second surface 18 or 20, respectively, of the first plate 10 in a region surrounding the opening thereby preventing the fixed end 5*a* being pulled into the channel. In yet another example, the holding element could be a stopper in the form of a knot, or series of knots, formed in the end of the suture 7 that is destined to be the fixed end 5*a*.

Figure 5A:
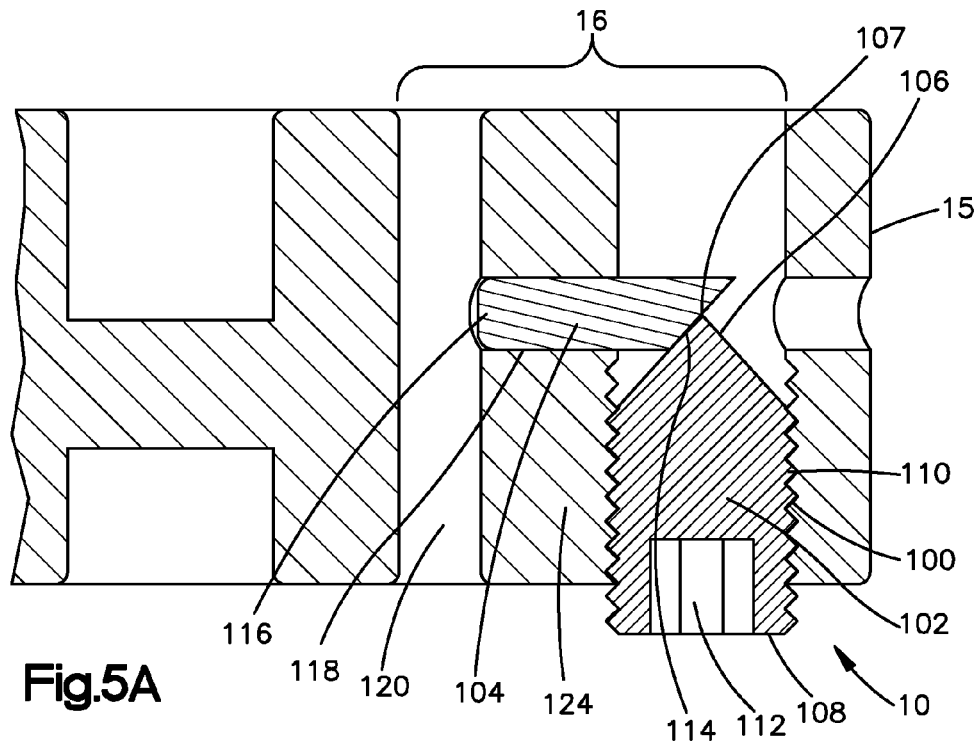
FIG. 5A is a sectional view of a holder of the first plate of FIG. 4, shown in an open configuration.
Figure 5B:
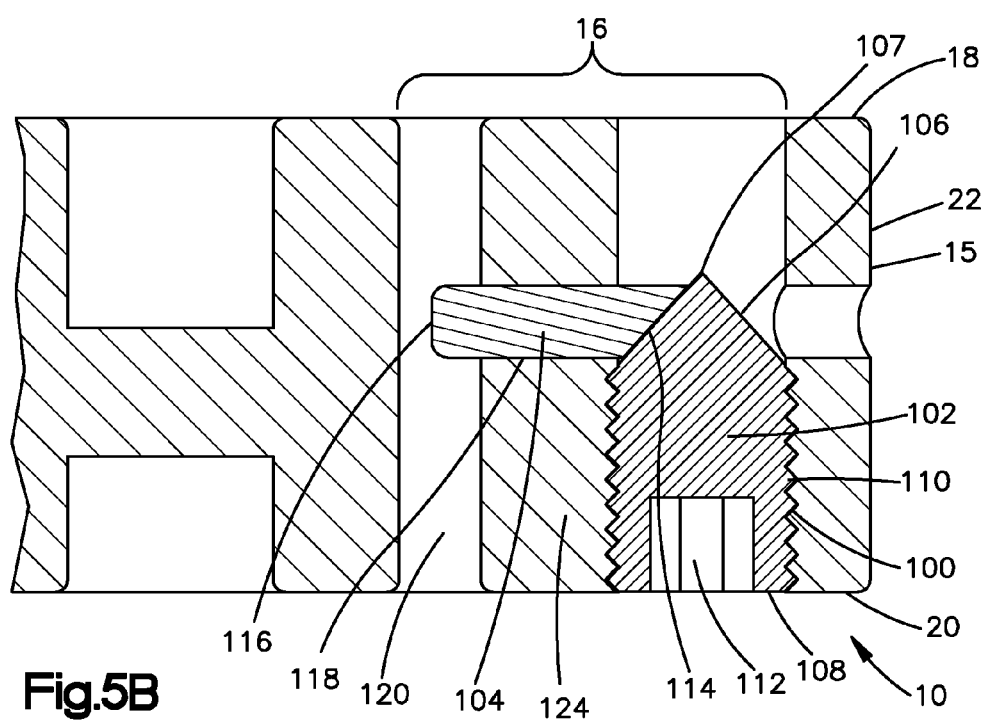
FIG. 5B is a sectional view of the holder of the first plate of FIG. 4, shown in a closed configuration.

Referring to FIGS. 5A and 5B, in an alternative embodiment of the first plate 10, the second holder 16 can include a set screw arrangement 100. The set screw arrangement 100 has a set screw 102 arranged to cause the holding of the suture 7 in position relative to the first plate 10. The set screw arrangement 100 can include a locking element 104. The set screw 102 is configured to interact with the locking element 104 to transition the locking element 104 to a closed configuration in which the locking element 104 is in a holding position in which it holds the suture 7 in position relative to the first plate 10. For instance, when in the holding position, the suture can be captured between the locking element 104 and the first plate body 15. With the set screw arrangement 100 the free end 5*b* of the suture 7 can be easily fixed in the first plate 10. The fixing could be during, for example, manufacture, an operation on a patient, etc. Thus, the second end 5*b* of the joining element 5 can be adjustably fixable to a fixing arrangement provided on one of the first or second plates 10 and 30, such as the first bone plate 10 as illustrated. The fixing arrangement can define a fixing region, for instance between the locking element and the first plate body 15, in which the second end 5*b* of the contractible element 5 is fixable to the first plate, for instance by one or more of a cam-lock of the type described above including a set screw and/or a clamp, or alternatively a knot or a crimp.

The set screw 102 has a first end 106 and a second end 108. The first plate 10 includes a set screw channel 110 that extends at least into, for instance through, the first plate body 15. In accordance with the illustrated embodiment, the set screw channel 110 can extend into the first surface 18 toward, for instance to, the second surface 20. The set screw channel 110 can be threaded such that the set screw 102 is configured to be positioned, for instance threadedly inserted, into the set screw channel 110 defined in the first plate 10. In a first end region adjacent the first end 106, the set screw 102 is tapered to a point 107 at the first end 106. The second end 108 is threaded to engage with a thread formed in the set screw channel 110. The threaded relationship between the second end 108 and the set screw channel 110 provides a resistance force, due to, for example, friction, which minimizes the likelihood that the set screw 102 may inadvertently or unexpectedly move relative to the set screw channel 110. The set screw 102 can define a cavity 112 that extends into the second end 108. The cavity 112 can be configured as a drive socket that is shaped to receive a drive tool, for example, a screwdriver. In use, a user engages the tool with the cavity 112 and uses it to rotate the set screw 102 to alter the position of the set screw 102 relative to the set screw channel 110, thereby driving the set screw 102 into and out of the set screw channel 110 in opposed rotative directions.

The locking element 104 has a trailing end 114 and a leading end 116 opposite the trailing end 114. The first plate 10 defines a locking element channel 118 that extends into the first plate body 15 along a direction that is perpendicular to the set screw channel 110. The locking element 104 is positioned in the locking element channel 118, such that the locking element channel 118 supports the locking element 104 and is shaped to guide the locking element 104 to and from the holding position. The locking element 104 extends from the trailing end 114 to the leading end 116 along the locking element channel 118. The trailing end 114 is located in the set screw channel 110 and the leading end 116 is located in a suture holding channel 120 defined in the first plate body 15. The trailing end 114 is configured to be engaged by the set screw 102 in order to move the locking element 104 relative to the locking element channel 118. The movement of the locking element 104 relative to the locking element channel 118 varies the amount of the leading end 116 located in the suture holding channel 120. The movement transitions the locking element 104 from a non-holding position, in which suture 7 positioned in the suture holding channel 120 is loosely received in the suture holding channel 120, to the holding position in which the holding end 5*b* of suture 7 positioned in the suture holding channel 120 is fixedly held relative to the first plate 10.

In the particular embodiment shown by FIGS. 5A and 5B, the leading end 116 is shaped in order to prevent inadvertent damage to the suture positioned and held in the suture holding channel 120. For example, the leading end 116 can be rounded. The trailing end 114 can be angled relative to a plane that extends perpendicular to a central axis of the locking element 104 that extends longitudinally from the leading end 116 to the trailing end 14. As shown, the entire trailing end 114 is angled relative to the plane. However, as the skilled person would of course understand, only a portion of the trailing end 114 may be angled. The angle of the trailing end 114 may be selected to correspond to the angle of the taper defined by the set screw 102 in the first end region. The correspondence of the angles may be selected in order to ensure a smooth engagement of the tapered first end region of the set screw 102 with the trailing end 114 and a smooth deployment of the locking element 114 to the holding position. The trailing end 114 can thus cam along the tapered first end region of the set screw as the set screw is driven to move relative to the set screw channel 110.

In the particular embodiment shown by FIGS. 5*a* and 5*b*, the set screw channel 110 and the suture holding channel 120 run parallel with respect to each other through the first plate 10. The first plate body 15 includes a wall 124 that separates and spaces apart the set screw channel 110 from the suture holding channel 120. Each of the set screw channel 110 and the suture holding channel 120 have openings into the respective channels formed on the first surface 18 and second surface 20. The locking element channel 118 runs perpendicular with respect to both the set screw channel 110 and the suture holding channel 120 through the first plate 10. The locking element channel 118 has a first portion defined by a first aperture 126 through the edge 22 into the set screw channel 110, a second portion which passes through the set screw channel 110 and a third portion defined by a second aperture 128 that passes through the wall 124 into the suture holding channel 120. The first aperture 126 is provided so that during assembly of the first plate 10, for example, during manufacture or in the operating room, the locking element 104 can be positioned in the locking element channel 118 through the set screw channel 110. With set screw 102 arranged in the set screw channel 110 and the locking element 104 arranged in the locking element channel, the relationship of the channels 110, 118 and 120 with respect to each other provides that movement of the set screw 102 along the set screw channel 110 in a first direction causes the locking element 104 to move along the locking element channel 118 toward the suture holding channel in a second direction which is perpendicular to the first direction resulting in an increase in the amount of the leading end 116 that is located in the suture holding channel 120. When a suture 7 is positioned in the suture holding channel 120, the amount of the leading end 116 is increased until the suture 7 is fixedly held in the first plate 10.

In operation, the set screw arrangement 100 is initially in an open configuration as shown by FIG. 5*a*. In the open configuration the suture 7 is inserted into the suture holding channel 120, and is capable of moving relative to the first plate 10 in the suture holding channel 120. A user then manipulates the set screw 102 to rotate in a first direction, which causes the set screw 102 to advance in the set screw channel 110, thereby causing the tapered first end 106 to abut the tapered trailing end 114 and cause the tapered trailing end 114 to cam along the tapered first end 106. As the tapered trailing end 114 cams along the tapered first end 106, the locking element 104 moves further into the suture holding channel 120. The engagement could be effected by a user inserting a driving instrument into the cavity 112 and rotating the set screw 102 such that the threaded second end 108 engages with the threaded portion of the set screw channel 110. The set screw 102 can be driven into the set screw channel 110 until the locking element 104 is moved to a closed configuration, whereby the suture 7 is captured in the suture holding channel 120 between the leading end 112 of the locking element 106 and an inner surface of the first plate body 15 that at least partially defines the suture holding channel 120. In this regard, the holding channel 120 can be referred to as an adjustment region in which the suture 7 is positionally adjustable relative to the first plate 10 that carries the second holder 16. An example of the closed configuration is shown by FIG. 5*b* with the suture 7 removed for simplicity.

Turning now to the pulley arrangement 13, FIGS. 1 and 4 show that the pulley arrangement 13 can define a plurality of pulleys 14 supported by the plate body 15. In the exemplary embodiment shown by FIGS. 1 and 4, the first plate has two pulleys 14. Each pulley 14 can include a first channel 14*a* that extends through the plate body 15 from the first surface 18 to the second surface 20, a second channel 14*c* that extends through the plate body 15 from the first surface 18 to the second surface 20, and a central axle 14*b* that is disposed between the first and second channels 14*a* and 14*c*. In one embodiment, the pulley 14 has a width measured along to the minor axis of the first plate 10 of 3 mm and a length measure along the major axis of the first plate 10 of 5 mm. However, as the skilled person would of course understand different lengths and widths are of course possible and may be different depending on the treatment for which the first plate 10 is to be used. The first channel 14*a* and second channel 14*c* are channels passing through the first plate 10 with apertures on the first and second surfaces 18 and 20. The axle 14*b* spaces apart or separates the first channel 14*a* from the second channel 14*c*. The axle 14*b* is shaped to provide a smooth transition from the first channel 14*a* to the second channel 14*c* in the direction of motion of the suture 7. The axle 14*b* can be fixedly attached to the plate body 15, such that the axle 14*b* has no moving parts. The smooth transition is provided to minimize fraying or otherwise damaging of the suture 7 during the initial adjustment to set the implant assembly 1 and during the self-contraction of the suture. In the preferred embodiment, the smooth transition is provided by the axle 14*b* having a curved surface in at least a region over which the suture 7 moves, in use. The axle 14*b* may be cylindrical and have a circular cross-section with respect to the direction of motion of the suture 7 to thereby provide the smooth transition over the axle 14*b*.

FIG. 6A shows a first embodiment of the axle 14*b*. The axle 14*b* has a cross-sectional dimension D in the direction from the first surface 18 to the second surface that can be the same as the plate thickness T. The cross-sectional dimension D can be a diameter or alternatively shaped cross-sectional dimension. However, as the skilled person would understand other cross-sectional dimensions can be chosen. The plate 10 shown in FIG. 4A is suitable for the treatment of the bone fracture of the sacrum. For such a treatment, the thickness T of the plate 10 is sufficient to support compressive forces that are to be applied to the iliac crest to maintain a reduction of the fractured sacrum S during bone healing. The plate thickness T identified as being suitable for such a treatment is 2 mm. In this regard, for this exemplary embodiment, the cross-sectional dimension of the axle 14*b* is 2 mm. However, as the skilled person would understand other plate thicknesses T and cross-sectional dimension D are of course possible for other treatments, in particular, where larger or smaller compressive forces are to be used. The axles 14*b* can be spaced along the major axis of the first plate 10, and can be aligned with each other such that their central axes are coincident with each other. The plate body 15 can include a divider wall 21 that is disposed between the axles 14*b*, such that a one of the axles 14*b* extends along a first direction from the divider wall 21 along the direction of the major axis, and another of the axles 14*b* extends along a second direction from the divider wall 21 along the direction of the major axis.

It should be appreciated that the first plate 10 can be constructed in accordance with any number of suitable embodiments. For instance referring now to FIG. 6B, the axle 14*b*' of the plate 10' constructed in accordance with a second embodiment can define a cross-sectional dimension D' along a direction from the first surface 18 to the second surface 20 that is smaller than the plate thickness T. The cross-sectional dimension D' can, for instance, be a diameter. The difference between the cross D' and thickness T may be chosen so that the crests of the curved outer surface defined by the axle 14*b*' that is disposed closest to the first and second surfaces 18 and 20, respectively, spaced a distance X from the respective first and second surfaces 18 and 20 of the first plate 10. The distance X can be larger than or equal to the cross-sectional dimension, such as a diameter, of the suture 7. The plate thickness T can be the same as the plate thickness described with reference to FIG. 4. That is the plate thickness T can be 2 mm. In one embodiment, the suture 7 may have a 0.5 mm cross-sectional dimension, for instance a diameter, and the cross-sectional dimension D' is 1 mm or less. In this exemplary embodiment, the center of the axle 14*b*' is located equidistant from the first and second surfaces 18 and 20, respectively. However, as the skilled person would understand the location of the center of the axle 14*b*' could of course be varied, and spaced closer to one of the first and second surfaces 18 and 20 than the other of the first and second surfaces 18 and 20. For example, should a cross-sectional dimension D' of 1.5 mm be desired, but the distance X of 0.5 mm be desired to accommodate the suture 7, then the center of the axle 14*b*' could be 0.75 mm from the second surface 20 and 1.25 mm from the first surface 18, The second holder 16 is configured to fixedly hold the free end 5*b* in position after an initial and desired compression has been set to hold the bone portion or portions together. In contrast to the first holder 9, the second holder 16 defines an end location through which the suture 7 is attached after having been woven through the pulley arrangement 13 of the first plate 10, which can define a first pulley arrangement, and a pulley arrangement 31 of the second plate 30 (see FIG. 7), which can define a second pulley arrangement. In one embodiment, the second holder 16 is a channel passing through the first plate body 15, from the first surface 18 to the second surface 20, and can define apertures on the first and second surfaces 18 and 20, respectively. The second surface 20, which is opposed to the first surface 18 that is destined to be a bone facing surface, and thus faces and can abut the lateral surface 12a of the first bone portion 12, has a bearing surface configured to receive a holding element that is arranged on the suture after a desired compression is set between the first and second plates. The holding element could be a stopper such as the crimp, knot or knots described above. The holding element could be a clamp or cleat arranged to receive a fixedly hold the free end 5b. Other holding elements capable of holding the free end 5b in a fixed position relative to second holder 16 are of course possible as the skilled person would understand. In a particular embodiment, the second holder 16 is the set screw arrangement 100 described above with reference to FIGS. 3A and 3B.

Referring now to FIG. 7, the second plate 30 can be constructed as described herein with respect to the first plate 10 with the exception that the second plate 30 can be devoid of holders, such that the second plate does not have a holder, i.e., neither a first holder 9 nor a second holder 16. That is, the second plate 30 has a second plate body 35 that defines a first surface 34, a second surface 36 opposite the first surface 34, and an edge 38 that is connected between the first surface 34 and the second surface 36. The second plate 30 includes a pulley arrangement 31 supported by the second plate body 35. The edge 22 defines an outer perimeter of the second plate 30, and the second plate 30 defines a plate thickness T that extends from the first surface 34 to the second surface 36. The second plate 30 can define a substantially cuboid shape with a rectangular cross-section whose corners are rounded to, for example, minimize soft tissue irritation. The second plate 30 can define a length as measured along its major axis as desired, such as approximately 20 mm. The second plate 30 can define a width measured along its minor axis as desired, such as approximately 7 mm. The thickness T as measured from the first surface 34 to the second surface 36 can be as desired, such as approximately 2 mm. However, as the skilled person would of course understand other dimensions are of course possible. For example, in treatment of a torn Syndesmosis joining the tibia to the fibula or a torn AC joint the length, width and depth could be approximately 12 mm, approximately 5 mm and approximately 1.5 mm, respectively. As the skilled person would understand, the second plate 30 may be adapted to comprise a holder of the type described with respect to the first plate 10 if desired.

The pulley arrangement 31 of the second plate 30 can have any number of pulleys 32 as desired, such as three pulleys 32. Each pulley 32 can include a first channel 32a that extends through the plate body 35 from the first surface 34 to the second surface 36, a second channel 32c that extends through the plate body 35 from the first surface 34 to the second surface 36, and a central axle 32b that is disposed between the first and second channels 32a and 32c. The pulleys 32 can be constructed as described above with regard to the pulleys 14 of the first plate 10. The difference between the first plate 10 and the second plate 30 being that the second plate 30 has an additional third pulley 32. That is, when the first plate 10 has two pulleys 14, the second plate has three pulleys 32. The relationship between the pulley arrangement 13 of the first plate 10 and the pulley arrangement 31 of the second plate is that the pulley arrangement 31 has one more pulley than the pulley arrangement 13. The axles 32b can be spaced along the major axis of the second plate 30, and can be aligned with each other such that their central axes are coincident with each other. The second plate body 35 can include a divider wall 39 that is disposed between adjacent ones of the pulleys 32.

Referring again to FIG. 1, a suture looping arrangement is shown in accordance with one embodiment. The fixed end 5a of the suture 7 can be fixed to the first plate 10 in the manner described above, and the suture 7 is looped from the first plate 10, through the second plate 30 and back to the first plate 10 relative to which it is to be held. The suture 7 can be again looped through the first plate 10, through the second plate 30, and back to the first plate 10. The suture 7 can be looped through the first plate 10 and through the second plate 30 and can extend back to the first plate 10 successively as many times as desired, depending for instance on the number of pulleys 14 and 32 of the first and second plates 10 and 30, respectively. In accordance with the illustrated embodiment, the suture 7 is looped through the second plate 30 three times, once around each pulley 32, and looped through the first plate 10 twice, once around each pulley 14. The suture 7 is looped through the pulleys 14 of the first plate 10 between successive loopings through the pulleys 32 of the second plate 30. Similarly, the suture is looped through the pulleys 32 of the second plate 30 between successive loopings through the pulleys 14 of the first plate 10.

When the suture 7 is looped through each of the pulleys 32 of the second plate 30, the suture 7 extends through one of the first and second channels 32a and 32c such as the first channel 32a in accordance with the illustrated embodiment, along a direction away from the first plate 10, around the axle 32b, and through the other of the first and second channels 32a and 32c, such as the second channel 32c in accordance with the illustrated embodiment, along a direction toward the first plate 10. The second channel 32c can be disposed superior with respect to the first channel 32a as illustrated. Thus, the suture 7 can extend from the first plate 10 through an inferior one of the first and second channels 32a and 32c along a direction away from the first plate 10, can loop around the axle 32b, and can extend through a superior one of the first and second channels 32a and 32c along a direction toward the first plate 10.

When the suture 7 is looped through each of the pulleys 14 of the first plate 10, the suture 7 extends through one of the first and second channels 14a and 14c such as the first channel 14a in accordance with the illustrated embodiment, along a direction away from the second plate 30, around the axle 14b, and through the other of the first and second channels 14a and 14c, such as the second channel 14c in accordance with the illustrated embodiment, along a direction toward the first plate 10. The second channel 14c can be disposed inferior with respect to the first channel 14a as illustrated. Thus, the suture 7 can extend from the second plate 30 through a superior one of the first and second channels 14a and 14c along a direction away from the second plate 30, can loop around the axle 14b, and can extend through an inferior one of the first and second channels 14a and 14c along a direction toward the second plate 30.

For implantation, the suture 7 is fixedly held by the first holder 9, successively looped through the pulleys 32 and 14, and is adjustably arranged relative to the second holder 16. The suture 7 is looped through the pulleys 14 and 32 of the pulley arrangements 14 and 31, respectively. In the exemplary arrangement shown by FIG. 1, the suture 7 is looped through the three pulleys of the pulley arrangement 31 and the two pulleys of the pulley arrangement 14. In the looping arrangement of suture 7 shown in FIG. 1, the suture 7 is looped through the pulleys 14 of the pulley arrangement 13 in the same manner. For example, the suture 7 is looped through each pulley in a clockwise direction. In this example, should the first plate 10 and second plate 30 be pulled apart or the suture 7 tensioned so that the suture 7 becomes taut, the parts of the suture running between the first and second plates 10 and 30, respectively, may be substantially parallel with respect to each other. As the skilled person would of course understand, the suture 7 may be looped clockwise, counter-clockwise, alternate between being looped clockwise and counter/clockwise, etc., through the pulleys 14 and 32 to achieve different suture looping arrangements as desired.

It should be appreciated that the alternative second plates can be constructed in accordance with any number of suitable alternative embodiments, for instance as shown in FIGS. 8A to 8E. The alternative second plate or plates 130, 130', 130", and 130''' can have many features in common with the second plate 30 with the exception that the alternative second plates can have alternative pulley arrangements. The dimensions of the alternative second plates 130, 130', 130", and 130''' can be as described in relation to the first plate 10 and the second plate 30. An embodiment of the alternative second plates 130, 130', 130", or 130''' can be interchangeably used or used instead of the second plate 30, as the skilled person would of course understand.

One form of the pulley arrangement of a first embodiment of the second plate 130 is shown in FIGS. 8A-B, where the pulley arrangement is provided by a shaft 138 located in a frame 132 that is defined by the second plate body 135. The frame 132 defines an inner surface that defines an opening 137 that extends through the frame body 135 from the first surface 134 to the second surface 136. The shaft 138 can divide the opening 137 into first and second regions. Similar to the pulley arrangements 13 and 31, the first region defines a first channel 37a and the second region defines a second channel 37b, each configured to receive and exit the suture 7 to and from the second plate 130. In accordance with the illustrated embodiment, the second channel 137b is disposed superior with respect to the first channel 137a. However, in the pulley arrangement of the first alternative embodiment of the second plate 130, there are no separate pulleys. Rather, the shaft 138 is shaped to provide a smooth transition from the first channel 137a to the second channel 137b in the direction of extension and motion of the suture 7. As can be seen from FIG. 9A, the shaft 138 may be cylindrical and have a circular cross-section with respect to the direction of extension and motion of the suture 7 to thereby provide the smooth transition over the entirety of the shaft 138. Thus, the shaft 138 can define an axle that the suture 7 is configured to loop around in the manner described above with respect to the pulley arrangement 31. Referring again to FIGS. 8A-E, the second plate 130, 130', 130", and 130''' can define first and second apertures 134a and 134b that extend into inner surfaces of the frame and spaced from each other along the direction of the major axis of the second plate body 135. The first and second apertures 134a and 134b can be shaped and dimensioned to hold and support the shaft 138 in the frame with an interference fit or any suitable alternative attachment as desired.

FIGS. 8C to 8E show pulley arrangements of the second, third and fourth embodiments of the second plate 130. The pulley arrangement of the second embodiment of the plate 130' can include one pulley 140a mounted on to the shaft 138. The pulley arrangement of the third embodiment of the plate 130" can have first and second pulleys 140a and 140b, respectively. The pulley arrangement of the fourth embodiment of the plate 130''' can have first, second, and third pulleys 140a, 140b and 140c, respectively. The pulleys 140a, 140b and 140c are arranged on the shaft 138 and spaced from each other along the length of the shaft. The pulleys 140a, 140b, 140c can be moveable, for instance rotatable, about the shaft 138, and thus rotatable with respect to the second plate body 135. Alternatively, the pulleys 140a, 140b, and 140c can be rotatably fixed to the shaft 138, and the shaft 138 can be rotatable with respect to the second plate body 135. Alternatively still, the pulleys 140a, 140b, and 140c can be rotatable with respect to the shaft 138, and the shaft 138 can be rotatable with respect to the second plate body 135. With respect to the pulley arrangement 13 and 31 and the one provided by the shaft 138, use of rotatable pulleys 140a, 140b and 140c may reduce the friction forces between the suture and the pulley arrangement as the skilled person would understand.

The pulleys 140a, 140b, 140c are supported by the shaft 138. In the second embodiment of the second plate 130' the pulley arrangement has one pulley 140a supported by the shaft 138. In the third embodiment of the second plate 130" two pulleys 140a, 140b are supported by the shaft 138. In the fourth embodiment of the second plate 130''' three pulleys 140a, 140b, 140c are supported by the shaft 138. The pulleys 140a, 140b, and 140c can be translatable along the length of the shaft 138, or can be translatably fixed to the shaft. As the skilled person would of course understand, different frames and pulley arrangements of the second plate 130 are of course possible. For example, in an alternate arrangement of the plate 130 with a pulley arrangement having one pulley or two pulleys, the frame could be sized such that, in the direction of the shaft, the opposed ends of the pulley arrangement are flush with respective inner edges of the frame. Further, the second plates 130 can have as many pulleys as desired.

Figure 9A:
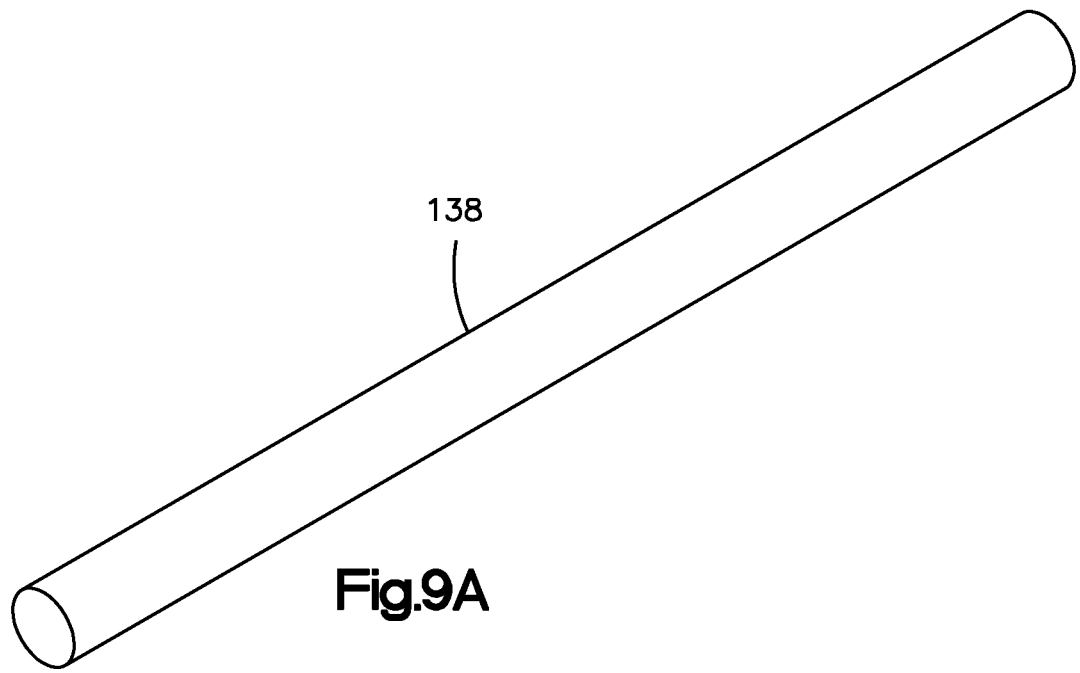
FIG. 9A is a perspective view of a shaft of the second plate constructed in accordance with the embodiments shown in FIGS. 8B to 8E.
Figure 9B:
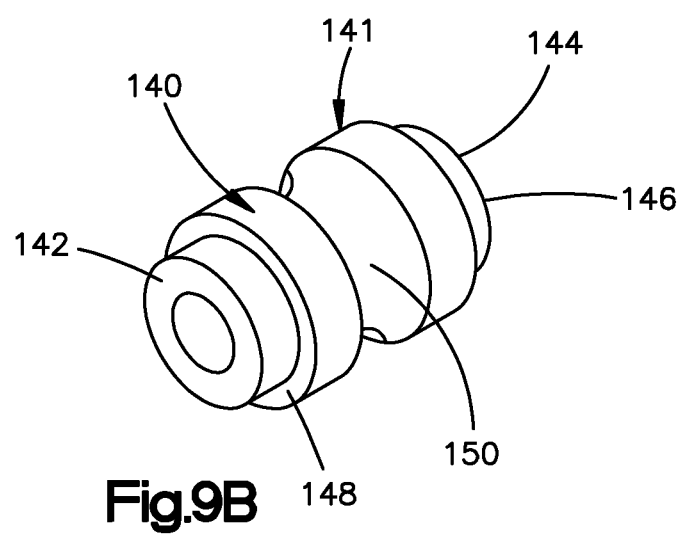
FIG. 9B shows a perspective view of a pulley of the second plate constructed in accordance with the embodiments shown in FIGS. 8C to 8E.

Referring to FIG. 9B, each of the pulleys 140 can define a pulley body 141 having a first end 142 and a second end 144 opposite the first end. The cross-sectional dimension of the pulley body 141 can vary from the first end 142 to the second end 144. For instance, the pulley body 141 can be substantially circular in cross-section relative to a first plane extending perpendicular to a central axis of the pulley 140, such that the cross-sectional dimension defines a diameter. The pulley body 141 can define a channel 146 that extends into one or both of the first and second ends 142 and 144. The channel 146 is shaped and dimensioned to receive an adjacent second or first end 144 or 142, respectively, of an adjacent pulley 140. That is, the diameter of the channel 146 is slightly larger than the diameter of the end that is to be received in the channel 146. In a region adjacent the first end 142, the diameter transitions from a first lesser diameter to a second diameter greater than the first diameter along a direction from the first end 142 toward the second end 144. The transition between the first and second diameters forms a shoulder 148, which is arranged to abut a second end of an adjacent pulley when a portion of the first end 142 is arranged in a channel of the second end of the adjacent pulley. The channel 146 can run through an entirety of the pulley body 141 from the first end 142 to the second end 144. The channel 146 has a channel axis which is concentric with a central axis of the pulley 140. The channel 146 is shaped and dimensioned so that the pulley 140 is rotatable about the shaft 138 when positioned thereon. Relative to the first plane, the inner surface of pulley body 141 that defines the channel 146 has a substantially cross-section dimensioned slightly larger than that of the shaft 138. For instance, inner surface of the pulley body 141 can be substantially circular, and the cross-sectional dimension of the inner surface of the pulley body 141 can be a diameter. The shaft 138 can also be cylindrical, such that the cross-sectional dimension of the shaft 138 can also be a diameter. The pulley body 141 can define a groove 150 that extends radially inward from an external surface of the pulley body 141 toward a central axis of the pulley 140 along which the pulley body is elongate, and about which the pulley 140 is rotatable. The groove can be disposed in a mid-region between the regions adjacent the first and second ends 140 and 142, respectively. The groove 150 is configured to receive the suture 7 as the suture 7 is looped around the pulley 140. In a plane extending from and parallel to the direction of the central axis, the groove 150 has a smooth or arc-shaped surface. The For instance, the surface of the groove 150 can define a distance, such as a diameter, that is measured in a direction parallel to the central axis between opposed sides of the groove and is larger than the diameter of the suture 7. Accordingly, the suture 7 is not inadvertently pinched in the groove 150, and undesired friction is not inadvertently introduced.

As the skilled person would of course understand, although the pulley arrangement 140 has been described with reference to its use as part of an embodiment of the second plate 130, the pulley arrangement 140 could be adapted for use with the pulley arrangement 13 of the first plate 10.

The plates 10, 30 and 130 and their respective elements can be manufactured from any suitable material, for example, metals such as titanium or steel or polymers such as Polyetheretherkeytone (PEEK) or reinforced PEEK.

Figure 10C:
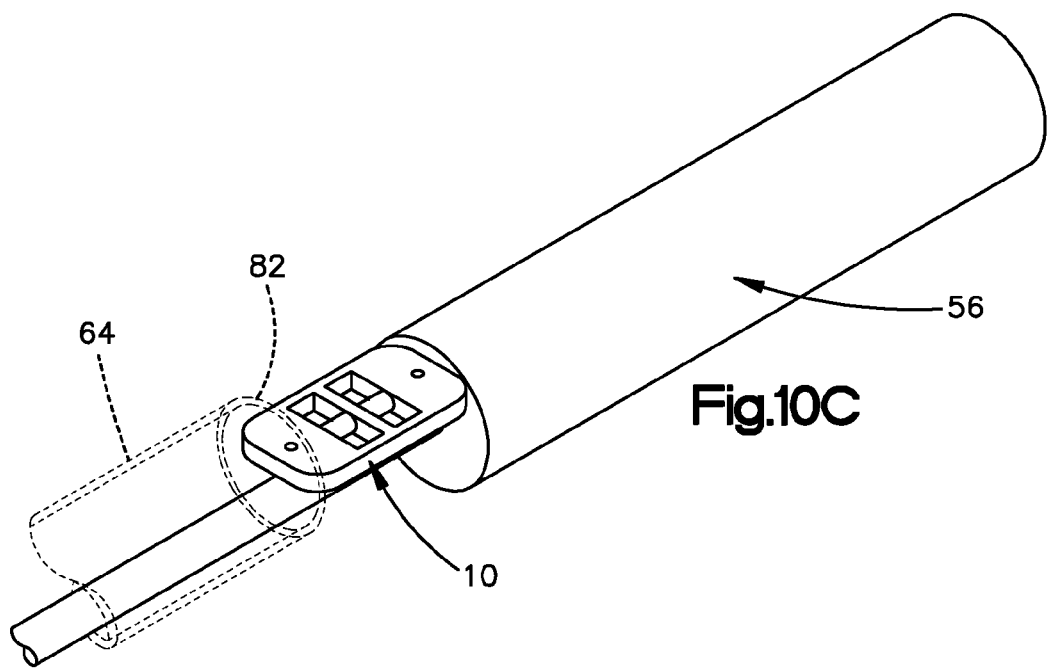
FIG. 10C is an enlarged perspective view of a second end of the instrument of FIG. 10A.
Figure 10D:
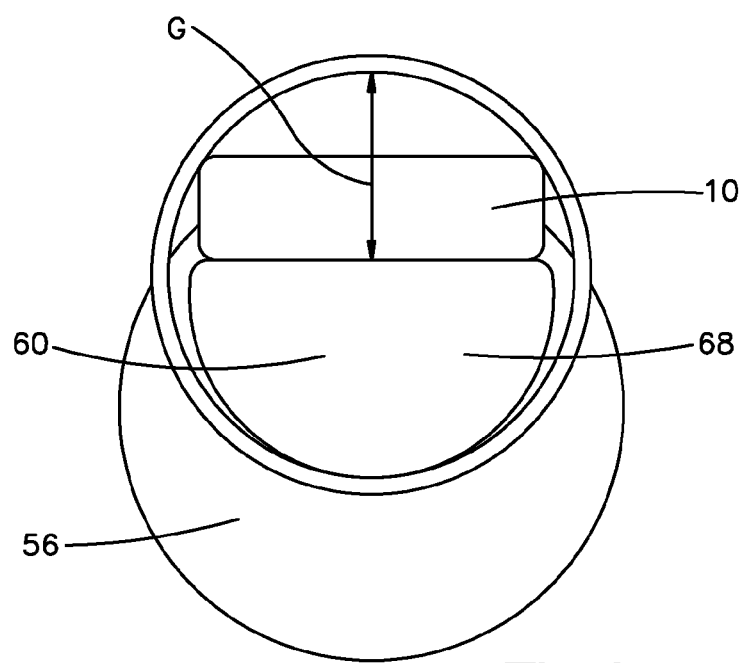
FIG. 10D is a front elevation view of the first end of the instrument shown in FIG. 10A.
Figure 11:
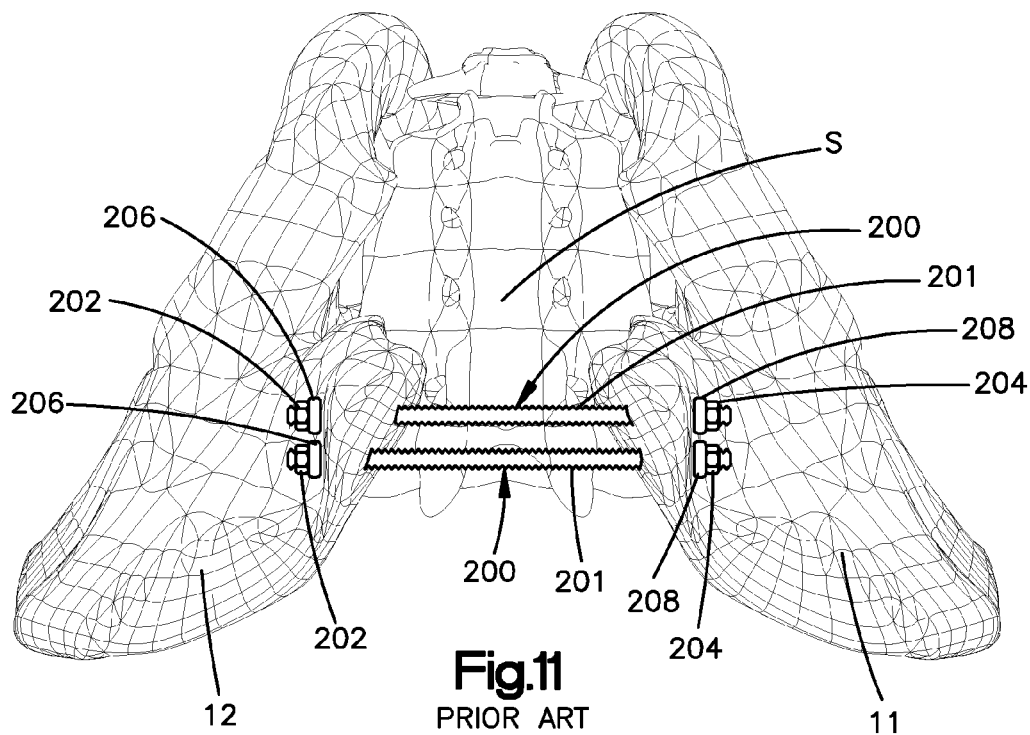
FIG. 11 shows an example of a prior art implant.
Figure 12:
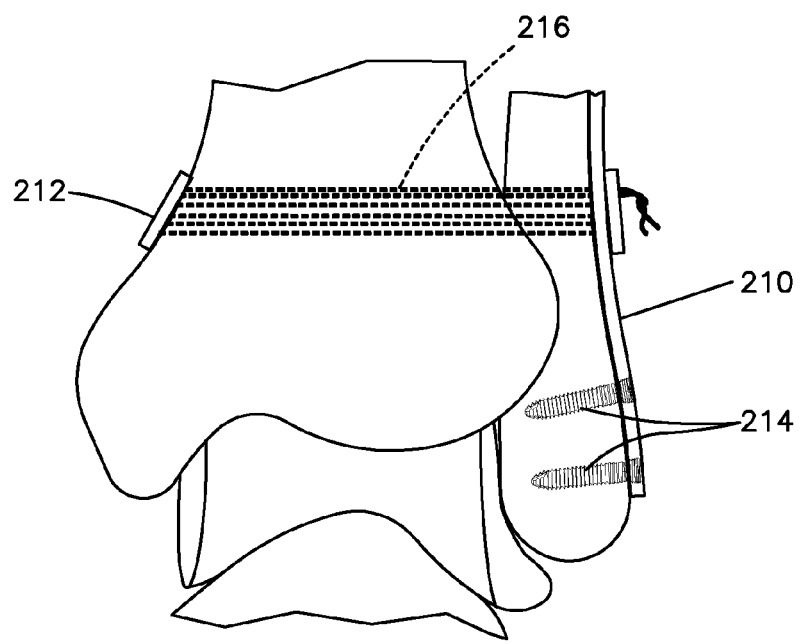
FIG. 12 shows another example of a prior art implant.
Figure 13:
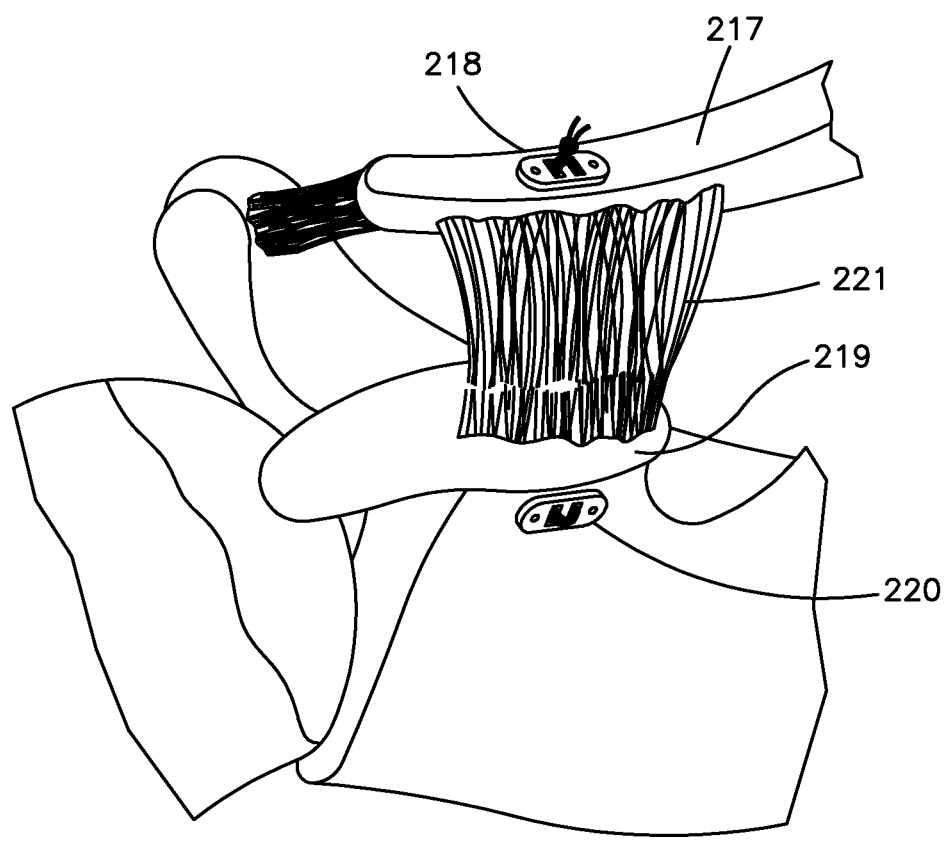
FIG. 13 shows yet another example of a prior art implant.

Referring now to FIGS. 10A to 10C, an instrument 50 includes a body 51 and a chamber 53 that extends into the body 51 and is configured to retain the implant assembly 1. The instrument 50 is configured to implant the implant assembly 1 into at least one bone or bones, and further includes a deployment element, such as a deployer 52, that is moveable between a first position and a second position relative to the chamber 53, the deployer 52 configured to deploy the implant assembly 1 during, for example, a surgical operation. The deployer 52 has an implant engaging member, such as a pusher 54 that is manipulable with a handle 56. The pusher 54 is spaced apart from the handle 56 with respect to an instrument axis IA running centrally along the instrument 50 by a connector 58. The connector 58 may be a rod that fixedly couples the handle 56 to the pusher 54 such that manipulation of the handle 56 is applied directly to the pusher 54. The deployer 52 has a first end 60 and a second end 62. The pusher 54 is located adjacent the first end 60 and the handle 56 is located adjacent the second end 62. Thus, when the implant assembly 1 is housed in the chamber 53, movement of the deployer 52 from the first position to the second position engages the pusher 54 with the implant assembly 1 to move at least part of the implant assembly 1, for instance one of the first and second plates 10 and 30, respectively, out of the chamber 53 through an opening of the chamber 53 at the first end 80.

The instrument body 51, and thus the instrument 50, can include a cover 64 that is elongate with respect to the instrument axis IA from a first end 80 of the body 51 to a second end 82 that is distal of the plate, which can be the first plate 10. The instrument 50 can include one or more radio-opaque elements arranged about the perimeter of the first end 80. As the skilled person would of course understand, the radio-opaque elements allow the first end 80 to be visible in a commonly available imaging system such C-Arm that provides X-ray images. Alternative arrangements, features or elements are of course possible to make the first end visible to other imaging systems.

The cover 64 is shaped and dimensioned to surround the pusher 54 and connector 58. The cover 64 as shown by FIGS. 10A to 10C is substantially tubular and can have a circular cross-section. However, as the skilled person would of course understand other shape covers 62 are of course possible. The cover 64 also has an outer diameter that is the same or substantially the same as the drill bit used in a surgical operation, which is described below in greater detail. For example, the drill bit may be 16.0 mm and the outer diameter of the cover 64 may be 15.5 mm to 16.0 mm. In other examples, the drill bit may be 4.5 mm in diameter, for example, when an AC joint is being treated or may be 3.5 mm in diameter when a Syndesmosis is being treated.

In an initial configuration, the cover 64 provides a housing for the pusher 54 and the connector 58 such that those elements are shielded from, for example, bodily tissue such as bone, skin, muscles, etc., during a positioning phase of a surgical operation, which is described in more detail below. As shown by FIGS. 10A to 10C, in the initial configuration, the cover 64 also houses the implant assembly 1, which for simplicity is shown without the suture 7 that is connected between the first plate 10 to the second plate 30 in the manner described above, substantially along the instrument axis IA as the skilled person would understand. The first plate 10 is located proximate to the handle 56 and the second end 82. The second plate 30 is located proximate to the pusher 54 and the first end 80. Thus the first plate 10 is disposed upstream with respect to the second plate 30. Otherwise stated, the first plate 10 is disposed closer to the handle 56 and the second end 82 than the second place 30. Similarly, the second plate 30 is disposed closer to the handle pusher 54 and the first end 80 than the first plate 10. The plates 10 and 30 are positioned such that their major axes extend substantially parallel to the instrument axis IA and their minor axes extend substantially perpendicular to the instrument axis IA. The suture 7 can be connected between the first and second plates 10 and 30 inside the instrument 50 in the manner described above. For instance, the fixed end 5a can be attached to the first holder 9, and the suture can be successively looped through the pulley arrangements 31 and 13. The free end 5b is arranged such that it is accessible through the second end 82. The free end 5b may be secured to the handle 56.

Referring to FIG. 10B, the pusher 54 will now be described in more detail. The pusher 54 has a pusher body 66 shaped to deploy the first and second plates 10 and 30, respectively, during a deployment phase of a surgical operation, which will be described in more detail below.

The pusher body 66 defines a forward engagement surface 68, an opposed end surface 70 that is disposed upstream of the engagement surface 68, a forward upper surface 72, a rearward upper surface 74 that extends upstream from the forward upper surface 72, and at least one peripheral surface 76 that is connected between the surfaces 68 and 70, and is further connected between the opposed lateral ends of the upper surfaces 72 and 74. For instance, the peripheral surface 76 can be partially cylindrical in shape. The body 66 runs along the instrument axis IA from a leading end, defined by the engagement surface 68, to a trailing end, defined by the end surface 70. The leading end is the first end 60 of the deployer 52. The surface 68 is an engagement surface arranged for engagement, for instance abutment, with the second plate 30 during a deployment phase, which is described in more detail below. In the initial configuration. The instrument 50 can define a distance along the instrument axis IA between the first end 60 or surface 68 and the first end 80 of the instrument 50 that is sufficient to allow the second plate 30 to extend longitudinally along the instrument axis IA and within the cover 64. In an exemplary embodiment, the second plate 30 is 20 mm in length and the distance between the first end 60 or surface 68 and the first end 80 is greater than 20 mm, for example, 25 mm to accommodate the second plate 30 within the cover pre-deployment. The engagement surface 68 can be a substantially planar surface that lies in a plane extending normal to the instrument axis IA. The trailing end can define a location at which the pusher 54 is coupled to the connector 58. The trailing end is defined by the surface 70. The surface 70 is a connection surface to which connector 58 is coupled. The connection surface 70 is substantially planar and lies in a plane extending transverse to the instrument axis IA.

The engagement surface 68 and the connection surface 70 are spaced apart from each other along the insertion axis IA by the surfaces 72, 74 and 76. The surfaces 72 and 74 can be substantially planar, and the surface 76 can be a curved surface that arcs from a first end to a second end defined by opposed edges of the planar surfaces 72 and 74, which extend from the leading end to the trailing end. The surface 72 can lie in a plane that is substantially parallel to the instrument axis IA. The surface 74 can lie in a plane which is angularly offset relative to the instrument axis IA. The surface 72 extends from the leading end to an intersection point at which the surface 72 meets the surface 74. From the intersection point, the surface 74 tapers towards the trailing end. In this regard, the body 66 is wedge-like. That is, the body 66 resembles a wedge having a curved base defined by the curved peripheral surface 76 and having its widest point at the leading end as defined by the distance between the planar surface 72 and the nadir of the curved peripheral surface 76 that transitions to its narrowest point at the trailing end due to the tapering of the surface 74.

The pusher 54 is shaped and dimensioned to be slideably moveable within an inner surface 78 of the cover 64 for deploying the first and second plates 10 and 30, respectively. The channel 53 of the instrument body 51 defines a gap G between the body 66 of the pusher 54 and the inner surface 78 of the cover 64. The gap G is sufficient to allow the suture 7 to be attached to the first and second plates 10 and 30 and ensure that interference of the pusher 54 with the suture 7 during the deployment phase described below is minimized. The gap G is sufficiently wide along a lateral direction that is perpendicular to the instrument axis IA so as to provide clearance that allows the first plate 10 to be removed from the instrument 50. The tapered surface 74 can provide a ramp that guides the first plate 10 through the gap G.

The peripheral surface 76 is shaped to guide the pusher 54 within the cover 58 relative to the instrument axis IA when the pusher 54 is moved. The surface 76 is arced to correspond to the arced inner surface 78 of the cover 58. With the pusher 54 located in the cover 64, the peripheral surface 76 can abut the inner surface 78 so as to guide the pusher 54 to translate relative to the cover 64 in a downstream direction (i.e., away from the second end 82) and upstream relative to the cover 64 in an upstream direction (i.e., toward the second end 82). The surface 74 is tapered to form a ramp. During the deployment phase described below, the ramp serves to urge the first plate 10 out of the cover 64.

A surgical method describing an operation in which an embodiment of the implantation system of the present invention is used to locate an implant assembly 1 on the first portion 12 and a second portion 11 of the Ilium bone for holding fractured portions of a sacrum bone S together for bone healing purposes (see FIG. 2A) will now be described. As the skilled person would of course understand, the surgical method described is by way of example, and other surgical methods are of course possible and within the scope of the invention. The skilled person would of course understand also that whilst the steps are described with reference to a bone and bone healing, the steps can of course be adapted to prepare any musculoskeletal tissue for treatment using the implant assembly 1. Examples of such treatment include: treatment of a torn ligament of a syndesmosis, for example, the syndesmosis between the tibia and fibula, and treatment of a torn ligament of the AC joint of the shoulder.

An implanted position of the implant assembly 1 on the first and second portions 12 and 11, respectively, of the Ilium can be seen in FIG. 2A. In the implanted position, a post-operative phase takes place during which, for example, healing, in particular of the bone, such as the sacral bone S, should occur. Several phases of operation can occur to position in the implant assembly 1 in the implanted position. An initial phase is a preparation phase during which holes are formed in the bone through which the implant assembly 1 may be positioned. In a positioning phase, the implant assembly 1 is located for deployment from within the instrument 50. A deployment phase is undertaken to place the second plate 30 on, for example, the second portion 11 of the right Ilium, and the first plate 10 on the first portion 12 of the left Ilium. With the first and second plates 10 and 30 in position, a setting phase is commenced during which an initial compression is set by manipulation of the free end 5b and the second holder 16. In this arrangement, the implant assembly 1 applies a compression to the first and second Ilium crests 12 and 11 for the purpose of maintaining compression across the sacrum S, resulting in a reduction of a fracture of the sacrum S and supporting bone healing of the Sacrum S The post operative phase then commences during which the self contracting suture 7 maintains the compressive force on the first and second plates 10 and 30, which consequentially apply a compressive pressure to the right and left Ilium in order to continue to hold fractured portions of the sacrum together under compression in support of bone healing.

The surgical method for treating a fractured sacrum will now be described in more detail.

Preparation Phase

During the preparation phase of the surgical operation, the musculoskeletal tissue is prepared for receiving the implant assembly 1. During part of the preparation phase, the fracture of the sacrum S is reduced with, for example, reduction forceps or any suitable alternative structure. After reduction of the fracture, Kirschner wires are placed across the sacroiliac joint for stabilization. A borehole is drilled in the first portion 12 of the left ilium, and another borehole is then drilled in the second portion 11 of the right ilium. These boreholes in the left and right ilium can interchanged according to preference, as the skilled person would understand. The boreholes may be drilled with the same drill bit in a single drilling step, for instance if the first and second plates 10 and 30 are similarly dimensioned, or in separate drilling steps, which can be with different drill bits if the first and second plates 10 and 30 are dimensioned differently from each other. The drill bit is removed leaving the bone reduced and prepared. The drill bit may be 16.0 mm in diameter. As the skilled person would of course understand, the size of the drill bit may larger or smaller than 16.0 mm and may be of a size selected as the size appropriate for a surgical operation. For example, the drill bit may be 4.5 mm in diameter, for example, when an AC joint is being treated and may be 3.5 mm in diameter when a Syndesmosis is being treated. The drill bit and resulting borehole can be of a dimension that is greater than the width of the first and second bone plates 10 and 30 along their minor axis, and less than the length of the first and second bone plates 10 and 30 along their major axis.

Positioning Phase

During the positioning phase, the surgeon inserts the instrument 50 containing the implant assembly 1 into the boreholes. As described above, the instrument 50 can include cutting flutes configured to form the boreholes in the bone. Once the boreholes have been formed, the surgeon can insert the cover 64, containing an implant assembly 1 first through one of the boreholes that extend through one of the first and second bone portions 12 and 11, respectively, and then through the other of the boreholes that extend through the other of the first and second bone portions 12 and 11. For instance, in accordance with the illustrated embodiment, the cover 64 is inserted first through the borehole of the first bone portion 12, and then through the borehole of the second bone portion 11. As described above, the diameter of the cover 64 can be substantially the same as the diameter of the drill bit to ensure that the cover 64 fits snugly in the boreholes. With the instrument 50, in particular, the cover 64, spanning from the borehole of the first, right bone portion 12 to the borehole of the second, left bone portion 11, an image can be taken of the sacrum S and iliac crests using any suitable imaging system. For instance, a C-Arm or other suitable imaging device can obtain and display an image that identifies the location of the instrument 50 relative to the boreholes. The instrument 50 may be repositioned as needed. As described above, the instrument 50 has one or more radio-opaque elements disposed at the first end 80. The C-Arm provides an image, for example, an X-ray image, that a surgeon can use ensure a desired position of the instrument 50 relative to the boreholes. For example, the image can show that the first end 80 is positioned in the one of the borehole, for example of the second bone portion 11 at the left ilium, such that subsequent deployment of the second plate 30 of the implant assembly 1 out the cover 64, and thus out the instrument 50, will cause the second plate 30 to be disposed adjacent the lateral surface 11a of the second bone portion 11, and further subsequent deployment of the first plate 10 out the cover 64, and thus out the instrument 50, will cause the first plate 10 to be disposed adjacent the lateral surface 12a of the first bone portion 12. For instance, the first end 80 can be positioned substantially flush with the lateral surface 11a of the second bone portion 11. Thus, the instrument 50 can include an external surface that is shaped and dimensioned to be passed through the boreholes. In accordance with one embodiment, the external surface can include drilling flutes for making boreholes in a bone, such as in the first and second bone portions 12 and 11.

Deployment Phase

With the instrument 50 appropriately aligned, the implant assembly 1 may be deployed. In a first step, the plate 30 is pushed out of the cover 64 using the deployer 52. To move the deployer 52 from the first position to the second position the handle 56 is manipulated by translating the handle 56 relative to the instrument axis IA. The handle 56 is translatable in the downstream direction from a first or initial configuration whereby the pusher 54 does not exert a deployment force onto either the first or second plates 10 and 30 that would cause the plate to be ejected from the instrument, to a deployed configuration whereby the pusher 54 exerts a deployment force onto either or both of the first and second plates 10 and 30 sufficient to eject the plate out the instrument 50. Thus, as the handle 56 is translated downstream, the pusher 54 is transitioned from the initial configuration to the deployed configuration, such that the first end 60 or engagement surface 68 of the pusher 54 is translated downstream along the instrument axis IA from a first distance away from the end 80 of the instrument 50 along the instrument axis IA to a second shorter distance from the end 80 along the instrument axis IA. The pusher 54, for instance at the engagement surface 68, engages, directly or indirectly, the second plate 30 during movement form the initial to the deployed configuration. The downstream movement of the pusher 54 causes the engagement surface to force, for instance push, the second plate 30 out of the cover 64 to a first deployment site, which can be the lateral surface 11a of the second bone portion 11.

In the deployed configuration, the surface 68 can be substantially flush with the end 80 of the instrument 50. The imaging device, for example a C-Arm, is then used to check that the second plate 30 has been deployed on the expected lateral side 11a of the left ilium bone portion 11, for instance such that the first surface 34 of the second plate body 35 is positioned facing the lateral side 11a. In accordance with one embodiment, the first surface 34 can abut the lateral side 11a, or can be spaced from the lateral side 11a so that the first surface 34 is positioned to abut the lateral side 34 when the first and second plates 10 and 30 are drawn toward each other after deployment.

With the deployer 54 in the deployed configuration, the surgeon can then draw the first end 80 of the instrument 50 from the borehole of the second bone portion 11 to the borehole of the first bone portion 12. In so doing, the suture 7, whose fixed end 5a has been pre-fastened to the first plate 10, and which has been pre-looped around the pulley arrangements 13 and 31, is pulled from the instrument 50 through the gap G into a location between the first and second bone portions 12 and 11. The instrument 50 is then removed from the borehole of the first bone portion 12 so that the first end 80 is disposed adjacent the lateral surface 12a of the first bone portion 12, such that the suture 7 extends through the borehole of the first bone portion 12. An image can again be taken of the instrument 50 to ensure that the first end 80 is positioned as desired. The handle 56 can then be retracted along the instrument axis IA, until the first implant 10 rides along the tapered upper surface 54 through the gap G to a position downstream of the engagement surface 68. Because the second plate 30 is tethered to the first plate via the suture 7, movement of the instrument away from the second plate 30 can draw the first plate 10 into the cover 64. Subsequent movement of the handle 56 downstream toward the first end 80 causes the handle to move to the deployed configuration whereby the pusher 54 exerts a deployment force onto the first plate 10 sufficient to eject the first plate 10 out the instrument 50, for instance out the opening 80, to a second deployment site, which is preferably different to the first deployment site. For instance, the second deployment site can be located at the lateral surface 12a of the first bone portion 12.

The surgeon then checks with the imaging device to ensure that the first plate 10 is in the expected position, with the first surface 18 positioned facing the lateral side 12a. In accordance with one embodiment, the first surface 18 can abut the lateral side 12a, or can be spaced from the lateral side 12a so that the first surface 18 is positioned to abut the lateral side 18 when the first and second plates 10 and 30 are drawn toward each other after deployment.

Setting Phase

With first and second plates 10 and 30 in the desired position such that the first surfaces 18 and 34 face the respective lateral surfaces 12a and 11a, the surgeon grips the free end 5b of the suture 7 that is looped between the first and second plates 10 and 30, either manually or via any suitable tensioning instrument, and sets a desired tension. In the event that the free end 5b of the suture 7 is attached to the handle 56, the surgeon can retract the handle 56 upstream along the instrument axis IA, or can manually translate the instrument 50 away from the second surface 20 of the first plate. The free end 5b is thus pulled through the second holder 16, while the locking element 104 is in the open configuration, thereby allowing the suture 7 to translate through the first plate 10, for instance through the suture holding channel 120 (see FIG. 5A). As the suture 7 translates through the first plate 10, the suture becomes tensioned along its length, including at the regions of the suture 7 that are looped around the first plate 10, the regions of the suture 7 that are looped around the second plate 30, and the regions of the suture 7 that extend between the first and second plates 10 and 30, respectively. Once a desired tension is reached in the suture 7 with the first surfaces 18 and 34 abutting the respective lateral surfaces 12a and 11a, respectively, or other suitable outer bone surfaces, the free end 5b is secured to the second holder 16. For instance, the locking element 104 can be moved to the closed configuration, thereby capturing the suture 7 in the first plate 10, for instance in the manner described with respect to FIG. 5B). It should be appreciated that while the first and second holders 9 and 16 are both included in the first plate 10, one of the first and second holders 9 and 16 can alternatively be included in the first plate 10 while the other of the first and second holders 16 can be included in the second plate 30. For instance, the first plate 10 can include the first holder 9, while the second plate 30 can include the second holder 16. Thus, the first fixed end 5a of the contractible element 5 has a can be fixed to one of the first and second plates 10 and 30, and the second free end 5b of the contractible element 5 can be adjustably fixable to a fixing arrangement provided on one of the first or second plates 10 and 30.

The desired tension thereby sets an initial compression that the first and second plates 10 and 30 apply to their respective parts of the bone, for example, the right and left ilium bone parts 12 and 11, respectively, to support bone healing. The desired tension may be identified by feel and experience. Alternatively a tension measuring device, such as a spring scale, may be attached to the suture 7 to reach a numerically desirable tension level. When the suture 7 has reached the desired tension level, the implant assembly 1 can be further imaged to ensure that the implant assembly 1 has been implanted as desired, (e.g., ensuring that plates 10 and 30 are positioned as desired, and the fracture of the sacrum S is reduced as desired, and that the suture 7 is positioned as desired). Adjustments to the implant assembly 1 can then be made as desired, and then the surgical procedure can be completed. The method steps can be repeated to implant a second one of the implant assemblies 1 as illustrated in FIG. 3, or any number of the implant assemblies 1 as desired.

Post Operative Phase

During the post operative phase, the self-contracting element 5 is operates to maintain the compression. As described above, this is achieved through an osmotic process in which the core of the element 5 expands thereby contracting the outer sheath surrounding the core with the net effect that the distance between the fixed end 5a and the free end 5b along the length of the element 5 is reduced. The reduction in the length of the element 5 counteracts any unwanted or undesired creep or stretching that may occur during bone healing, for instance as the ilium portions 12 and 11 move relative to the first and second plates 10 and 30, respectively, for instance toward each other. In so doing, the initial compression is substantially maintained. For instance, in some cases, the increase in compression of the element 5 can greater than the migration of the ilium portions 12 and 11 relative to the first and second plates 10 and 30, such that the compression in the element 5 may be increased during the post operative phase. In other cases, the increase in compression of the element 5 is less than the migration of the ilium portions 12 and 11 relative to the first and second plates 10 and 30, such that the compression in the element 5 may be decreased during the post-operative phase. In either case, the element 5 in combination with the plates 10, 30 can cooperate to ensure that a satisfactory compression is maintained at the fracture location of the sacrum S to support bone healing.

If desired, the first plate 10 and second plate 30 and the element 5 may be removed once the treatment has finished and the fracture has healed to a desired degree. This may be done through a first incision on the left side of the ilium and a second incision of the right side of the ilium. The suture 7 can be severed as desired to allow the first and second plates 10 and 30, respectively, to be withdrawn through the respective incisions.

The above description has described how embodiments of the implant assembly 1 may be used to support bone healing of a fractured sacrum S in accordance with certain embodiments. However, as the skilled person would of course understand, the implantation system having an implant or plurality of implant assemblies 1 and an instrument or instruments 50 could be used to support bone healing, ligament healing, tendon healing. In other surgical operations a torn AC-CC joint or a torn syndesmosis of the tibulafibula joint may be treated.

It will of course be understood that this description is by way of example only; alterations and modifications may be made to the described embodiment without departing from the scope of the invention as defined in the claims.

The invention claimed is:

1. An implant assembly comprising:
   a suture;
   a first implant member having a thickness and including:
     a first channel that extends through the thickness of the first implant member along a first channel axis, wherein the first channel fixedly receives the suture;
     a second channel that extends through the thickness of the first implant member along a second channel axis, the second channel configured to adjustably hold the suture, wherein the first and second channels are spaced from each other and circumferentially closed to each other in their respective entireties with respect to a direction that intersects both the first and second channel axes; and
     a locking element translatable between a holding position configured to hold the suture in the second channel, and a non-holding position configured to release the suture such that the suture is translatable in the second channel; and a pulley arrangement disposed between the first and second channels, the pulley arrangement including:

a plurality of openings that 1) extend through the thickness of the first implant member and 2) are elongate along a first direction perpendicular to the thickness of the first implant member; and a plurality of axles that extend through respective ones of the openings along a direction perpendicular to both the first direction and the thickness of the first implant member, the axles dividing the openings into first channels and second channels, and a second implant member configured to be positioned opposite the first implant member, wherein the suture is woven about each of the axles and extends through each of the first and second channels of each of the plurality of openings so as to attach to the second implant member.

2. The implant assembly of claim 1, further comprising a linear locking element channel that is open to the second channel, wherein the locking element is linearly translatable between the holding position and the non-holding position in the locking element channel.

3. The implant assembly of claim 2, further comprising a third channel configured to receive a set screw that is configured to urge the locking element from the non-holding position to the holding position.

4. The implant assembly of claim 3, wherein the third channel runs parallel to the second channel, and the locking element channels runs transverse to both the second and third channels.

5. The implant assembly of claim 1, wherein the axles are cylindrical.

6. The implant assembly of claim 5, wherein the first implant member has one more axle than the second implant member.

7. The implant assembly of claim 1, the second implant member further comprising:

a second pulley arrangement including:

a plurality of second openings that 1) extend through a thickness of the second implant member and 2) are elongate along a respective first direction perpendicular to the thickness of the second implant member; and a plurality of second axles that extend through respective ones of the second openings along a direction perpendicular to both the respective first direction and the thickness of the second implant member, the second axles dividing the second openings into respective first channels and respective second channels, and wherein the suture is woven about each of the axles of the first and second implant members and through the first and second channels of each of the plurality of openings of each of the first and second implant members so as to secure the first and second implant members to each other.

8. An implant system comprising:

the implant assembly of claim 7; and an instrument including:

a chamber that houses the implant assembly, and an external surface shaped and dimensioned to be passed through boreholes formed in a bone; and a deployer disposed between the first and second implant members in the chamber, the deployer having a forward engagement surface and a rearwardly extending tapered surface, wherein the deployer is 1) movable in a forward direction to thereby cause the engagement surface to push the second implant member out of the chamber, 2) subsequently retractable in a rearward direction in the chamber so as to cause the first implant member to ride along the tapered surface to a position forward of the engagement surface in the chamber, and 3) subsequently movable in the forward direction to thereby cause the engagement surface to push the first implant member out of the chamber.

9. An implant system comprising:

the implant assembly of claim 1; and an instrument including:

a chamber that houses the implant assembly, and an external surface shaped and dimensioned to be passed through boreholes formed in a bone; and a deployer disposed between the first and second implant members in the chamber, the deployer having a forward engagement surface and a rearwardly extending tapered surface, wherein the deployer is 1) movable in a forward direction to thereby cause the engagement surface to push the second implant member out of the chamber, 2) subsequently retractable in a rearward direction in the chamber so as to cause the first implant member to ride along the tapered surface to a position forward of the engagement surface, and 3) subsequently movable in the forward direction to thereby cause the engagement surface to push the first implant member out of the chamber.

* * * * *